US011033665B2

(12) United States Patent
Rhee et al.

(10) Patent No.: US 11,033,665 B2
(45) Date of Patent: Jun. 15, 2021

(54) MODIFIED VERESS NEEDLE ASSEMBLY FOR TENSION PNEUMOTHORAX DECOMPRESSION

(71) Applicant: The Arizona Board of Regents on Behalf of the University of Arizona, Tucson, AZ (US)

(72) Inventors: Peter Rhee, Tucson, AZ (US); Andrew Tang, Tucson, AZ (US); Kevin Okarski, Tucson, AZ (US)

(73) Assignee: The Arizona Board of Regents on Behalf of The University of Arizona, Tucson, AZ (US)

( * ) Notice: Subject to any disclaimer, the term of this patent is extended or adjusted under 35 U.S.C. 154(b) by 154 days.

(21) Appl. No.: 16/346,840

(22) PCT Filed: Nov. 3, 2017

(86) PCT No.: PCT/US2017/060019
§ 371 (c)(1),
(2) Date: May 1, 2019

(87) PCT Pub. No.: WO2018/085706
PCT Pub. Date: May 11, 2018

(65) Prior Publication Data
US 2019/0314561 A1 Oct. 17, 2019

Related U.S. Application Data

(60) Provisional application No. 62/418,007, filed on Nov. 4, 2016.

(51) Int. Cl.
*A61M 1/04* (2006.01)
*A61B 17/34* (2006.01)
*A61M 39/24* (2006.01)

(52) U.S. Cl.
CPC ............ *A61M 1/04* (2013.01); *A61B 17/3496* (2013.01); *A61M 39/24* (2013.01);
(Continued)

(58) Field of Classification Search
CPC .. A61M 1/04; A61B 17/3474; A61B 17/3494; A61B 2017/3492; A61B 17/3496
See application file for complete search history.

(56) References Cited

U.S. PATENT DOCUMENTS

| | | | |
|---|---|---|---|
| 2,623,521 | A | 12/1952 | Shaw |
| 3,090,384 | A | 5/1963 | Baldwin |

(Continued)

FOREIGN PATENT DOCUMENTS

| | | |
|---|---|---|
| CN | 203425005 | 2/2014 |
| WO | WO 83/00429 | 2/1983 |
| WO | WO 09/068661 | 6/2009 |

OTHER PUBLICATIONS

Eckstein et al., "Needle thoracostomy in the prehospital setting," *Prehosp Emerg Care*, Apr.-Jun. 1998; 2(2):132-5.

(Continued)

*Primary Examiner* — Kevin C Sirmons
*Assistant Examiner* — Joshua Parker Reddington
(74) *Attorney, Agent, or Firm* — Klarquist Sparkman, LLP

(57) ABSTRACT

A needle assembly includes an outer cannula having a distal end portion, the distal end portion comprising a sharp bevel facilitating insertion of the needle assembly into a subject. The needle assembly further includes an inner cannula slidably disposed coaxial in the lumen of the outer cannula and movable between an extended position and a retracted position, the inner cannula having a blunt distal end portion extending beyond the sharp bevel of the outer cannula whenever the inner cannula is in the extended position. The (Continued)

needle assembly further includes a bias coupled to the inner cannula in a manner favoring automatic positioning of the inner cannula at the extended position. The needle assembly includes a valve located in fluid communication with the lumen of the inner cannula to allow fluid to exit the subject through the inner cannula, and to prevent ingress of fluid into the subject.

19 Claims, 20 Drawing Sheets

(52) U.S. Cl.
CPC ..... *A61B 17/3474* (2013.01); *A61B 2017/347* (2013.01); *A61B 2017/3492* (2013.01); *A61M 2039/2406* (2013.01)

(56) References Cited

U.S. PATENT DOCUMENTS

| | | | |
|---|---|---|---|
| 4,403,617 A | 9/1983 | Tretlinyak | |
| 4,447,235 A | 5/1984 | Clarke | |
| 4,702,260 A | 10/1987 | Wang | |
| 4,813,941 A | 3/1989 | Shea | |
| 4,869,717 A | 9/1989 | Adair | |
| 5,030,207 A | 7/1991 | Mersch | |
| 5,098,388 A | 3/1992 | Kulkashi et al. | |
| 5,104,381 A | 4/1992 | Gresl | |
| 5,137,520 A * | 8/1992 | Maxson | A61M 25/02 128/DIG. 26 |
| 5,217,438 A | 6/1993 | Davis et al. | |
| 5,217,441 A * | 6/1993 | Shichman | A61B 17/3403 604/164.01 |
| 5,300,046 A | 4/1994 | Scarfone et al. | |
| 5,334,159 A * | 8/1994 | Turkel | A61B 17/3496 604/158 |
| 5,343,853 A | 9/1994 | Komi | |
| 5,354,288 A | 10/1994 | Cosgrove | |
| 5,374,252 A | 12/1994 | Banks | |
| 5,380,290 A | 1/1995 | Makower | |
| 5,560,373 A | 10/1996 | De Santis | |
| 5,685,852 A | 11/1997 | Turkel | |
| 5,725,506 A | 3/1998 | Freeman | |
| 5,971,960 A | 10/1999 | Flom et al. | |
| 5,997,486 A | 12/1999 | Burek | |
| 6,077,179 A | 6/2000 | Liechty, II | |
| 6,447,483 B1 | 9/2002 | Steube | |
| 6,702,790 B1 | 3/2004 | Ross | |
| 6,742,519 B2 | 6/2004 | Turnbull | |
| 6,770,070 B1 | 8/2004 | Balbierz | |
| 6,869,430 B2 | 3/2005 | Balbierz | |
| 7,229,433 B2 | 6/2007 | Mullen | |
| 7,591,807 B2 | 9/2009 | Villette | |
| 8,568,422 B2 | 10/2013 | Morlet | |
| 2006/0122458 A1 | 6/2006 | Bleich | |
| 2008/0091174 A1 * | 4/2008 | Alam | A61M 39/24 604/541 |
| 2008/0172033 A1 | 7/2008 | Keith | |
| 2009/0264826 A1 | 10/2009 | Thompson | |
| 2010/0087828 A1 | 4/2010 | Krueger | |
| 2010/0331883 A1 | 12/2010 | Schmitz | |
| 2011/0118658 A1 | 5/2011 | Smith | |
| 2013/0310750 A1 * | 11/2013 | Hopman | A61M 1/008 604/159 |
| 2013/0310752 A1 | 11/2013 | Kawaura | |
| 2014/0046303 A1 * | 2/2014 | Donaldson | A61B 17/3415 604/540 |
| 2016/0022312 A1 | 1/2016 | Tang | |
| 2016/0143662 A1 | 5/2016 | Mulier | |
| 2017/0087310 A1 | 3/2017 | Clement | |

OTHER PUBLICATIONS

International Search Report dated Jun. 10, 2014, by the ISA/FIPS, for International Patent Application No. PCT/US2014/020027, 2 pp.

International Search Report and Written Opinion issued by the International Searching Authority dated Mar. 28, 2018, for PCT/US2017/060019.

Janicki, "The new sensor-equipped veress needle," *The Journal of the American Association of Gynecologic Laparoscopists*, Feb. 1994, vol. 1, Issue 2, pp. 154-156.

Jaskille et al., "A Portable Handpump Is Effective in the Evacuation of Hemothorax in a Swine Model of Penetrating Chest Injury," *Journal of Trauma Injury, Infection, and Critical Care*, vol. 5(5), pp. 864-868, Nov. 2003.

Warner et al., "Paramedic use of needle thoracostomy in the prehospital environment," *Prehosp Emerg Care*, Apr.-Jun. 2008; 12(2):162-168.

\* cited by examiner

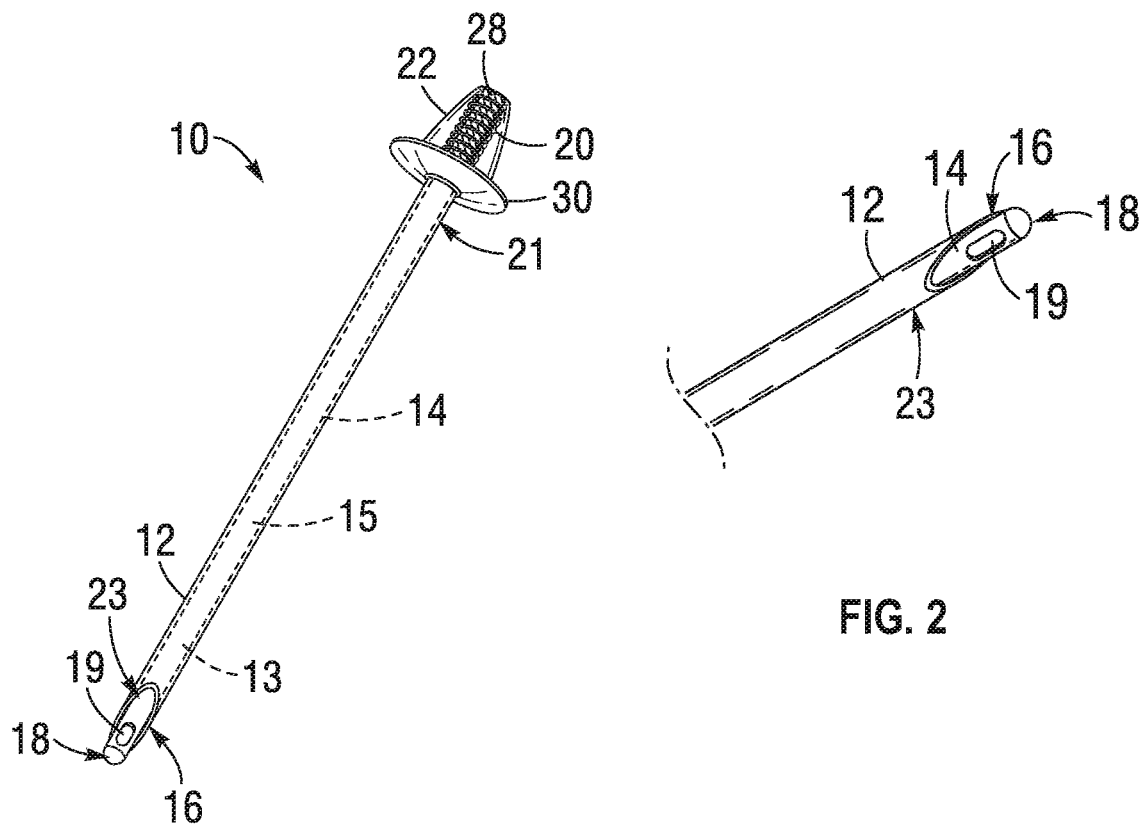
FIG. 1
FIG. 2
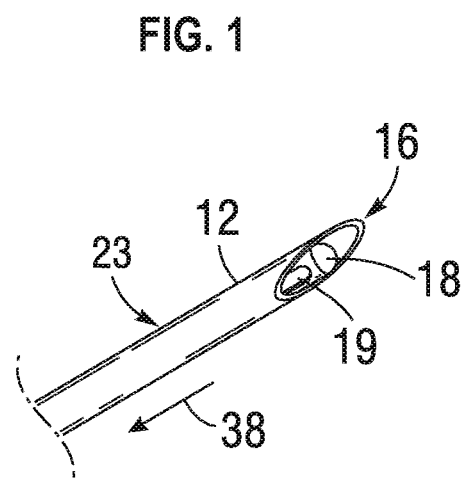
FIG. 3
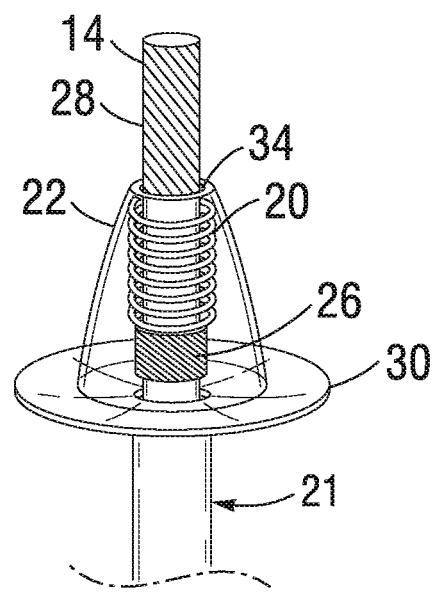
FIG. 5

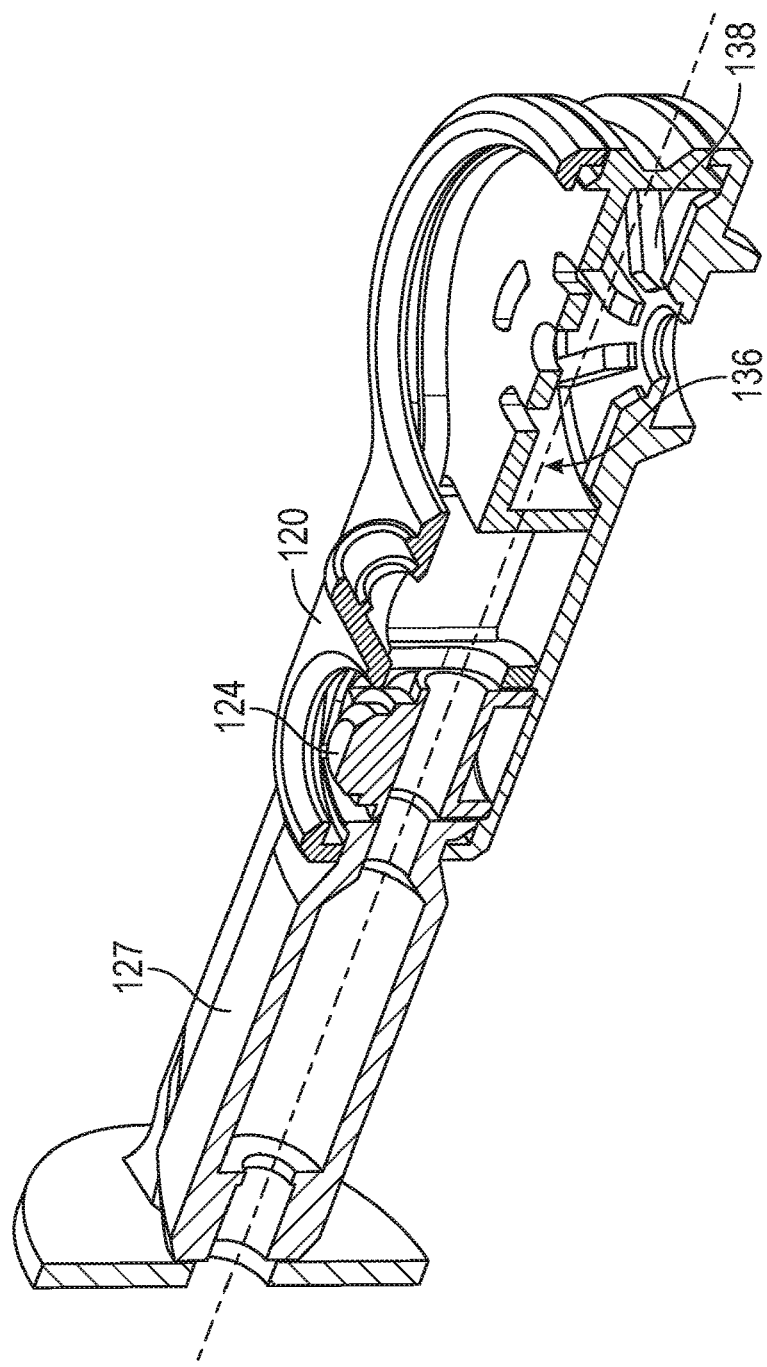
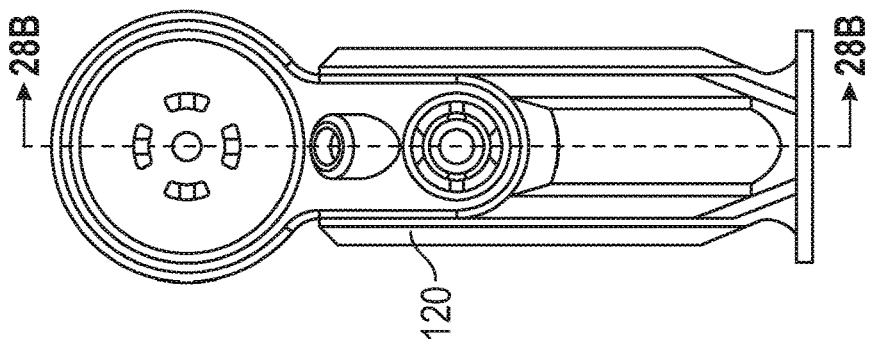
FIG. 28B
FIG. 28A

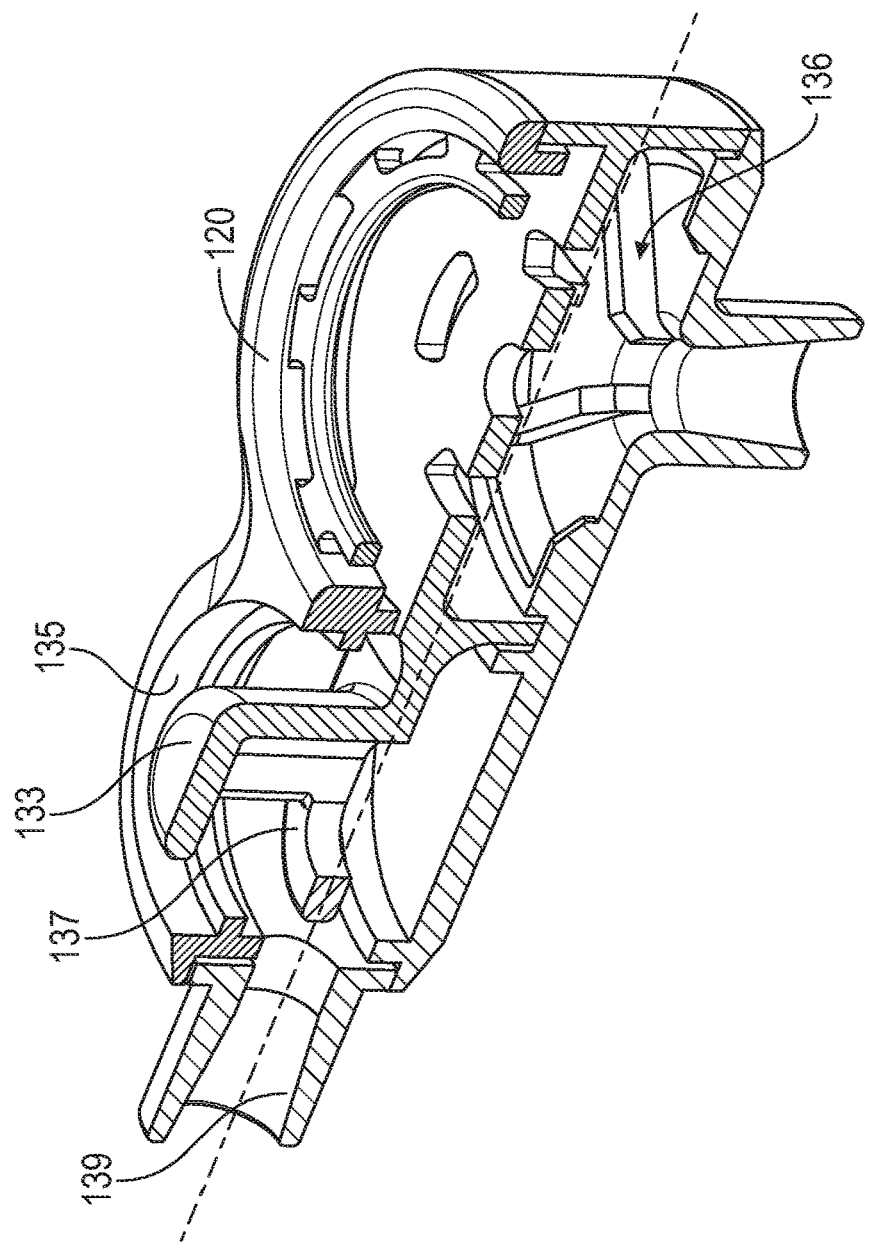
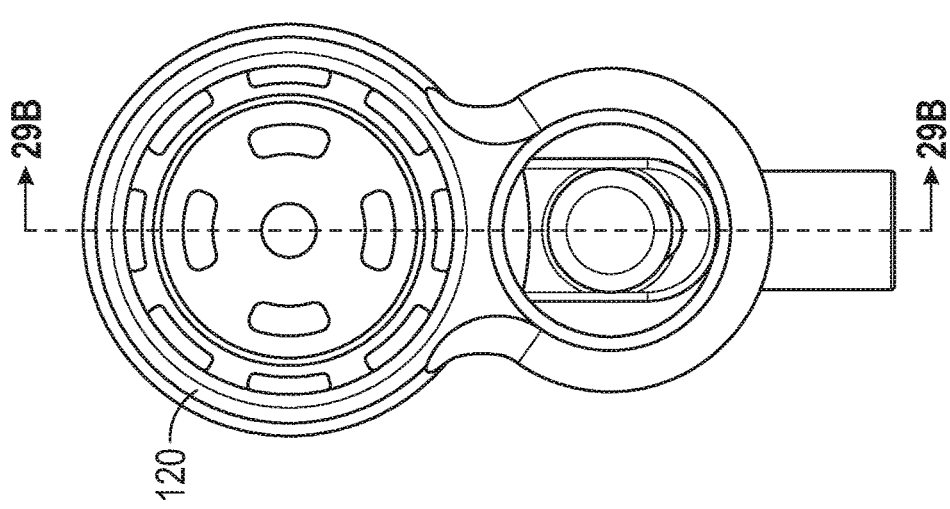
FIG. 29B
FIG. 29A

MODIFIED VERESS NEEDLE ASSEMBLY FOR TENSION PNEUMOTHORAX DECOMPRESSION

CROSS REFERENCE TO RELATED APPLICATIONS

This is the U.S. National Stage of International Application No. PCT/US2017/060019, filed Nov. 3, 2017, which was published in English under PCT Article 21(2), which in turn claims the benefit of U.S. Provisional Application No. 62/418,007, filed Nov. 4, 2016. The disclosures of International Application No. PCT/US2017/060019 and U.S. Provisional Application No. 62/418,007 are incorporated herein by reference in their entirety.

FIELD

The present disclosure pertains to needle assemblies for treating, for example, tension pneumothorax.

BACKGROUND

Tension pneumothorax is a life-threatening condition that is present in 0.2-1.7% of civilian trauma patients and up to 4% of battlefield casualties. This condition can result from a laceration of the lung, creating a parenchymal air leak with no means of evacuation. Consequently, the patient can manifest with severe hypoxia, hypercarbia, and/or cardiovascular collapse as increasing pressure in the hemithorax creates ipsilateral lung collapse and impedance of venous return to the heart.

Previous data from the Vietnam War suggested that up to 33% of preventable deaths on the battlefield resulted from tension pneumothorax. In civilian patients, the reported incidence of tension pneumothorax varies from 0.2% to 1.7%. In some cases, about 1.5% of blunt trauma patients can undergo needle decompression for suspected tension pneumothorax.

Despite its lethality, tension pneumothorax can be reversed with effective thoracic decompression. The current standard pre-hospital treatment of tension pneumothorax, as described in the $9^{th}$ edition of the Advance Trauma Life Support (ATLS) Student Course manual, is immediate decompression by inserting a large-caliber needle, most commonly a 5-cm 14-gauge angiocatheter, into the second intercostal space in the mid-clavicular line of the affected hemithorax. However, this technique has been repeatedly shown to be ineffective and unsafe, with failure rates ranging from about 40% to about 64%. Extrathoracic catheter placement and catheter kinking are the most commonly observed technical failures. Accordingly, improvements to devices and methods of treating tension pneumothorax are desirable.

SUMMARY

Certain embodiments of the disclosure pertain to needle assemblies for treating, for example, tension pneumothorax. In a representative embodiment, a needle assembly comprises an outer cannula defining a lumen and having a proximal end portion and a distal end portion. The distal end portion comprises a sharp bevel facilitating insertion of the needle assembly into a subject, and the proximal end portion is received in a housing. The needle assembly further includes an inner cannula slidably disposed coaxially in the lumen of the outer cannula and being movable relative to the outer cannula between an extended position and a retracted position. The inner cannula defines a respective lumen and has a blunt distal end portion and a proximal portion. The blunt distal end portion extends beyond the sharp bevel of the outer cannula whenever the inner cannula is in the extended position, and is at least partially retracted within the lumen of the outer cannula whenever the inner cannula is in the retracted position. The proximal end portion of the inner cannula is received in the housing. The needle assembly further includes a bias situated in the housing and coupled to the inner cannula and the outer cannula in a manner favoring automatic positioning of the inner cannula at the extended position unless the blunt distal end is experiencing a sufficient force to move the inner cannula to the retracted position. The needle assembly further comprises a valve located in the housing and in fluid communication with the lumen of the inner cannula, and configured when inserted into a subject to allow fluid to exit the subject through the inner cannula. The valve is further configured to prevent ingress of fluid into the subject when a pressure inside the subject is lower than an ambient pressure.

In another representative embodiment, a method comprises activating a locking mechanism of a Veress-type needle assembly to allow a biased inner cannula of the needle assembly to move from an extended position to a retracted position through an outer cannula through which the inner cannula is disposed. The outer cannula includes a proximal end portion and a distal end portion, and the distal end portion comprises a sharp bevel which is exposed when the inner cannula is in the retracted position. The method further comprises advancing the needle assembly into a thoracic cavity of a living subject such that the inner cannula moves from the extended position to the retracted position through the outer cannula exposing the sharp bevel. The method further comprises halting advancement of the needle assembly into the thoracic cavity when the inner cannula moves from the retracted position to the extended position.

In another representative embodiment, a method of making a needle assembly comprises inserting an inner cannula through a lumen of an outer cannula such that the inner cannula is slidably disposed coaxially in the lumen of the outer cannula and movable relative to the outer cannula between an extended position and a retracted position. The outer cannula has a proximal end portion and a distal end portion, and the distal end portion comprises a sharp bevel facilitating insertion of the outer cannula into a subject. The inner cannula defines a respective lumen and has a blunt distal end portion and a proximal portion. The blunt distal end portion extends beyond the sharp bevel of the outer cannula whenever the inner cannula is in the extended position, and is at least partially retracted within the lumen of the outer cannula whenever the inner cannula is in the retracted position. The method further comprises coupling a bias to the inner cannula in a manner favoring automatic positioning of the inner cannula at the extended position unless the blunt distal end is experiencing a sufficient force to move the inner cannula to the retracted position. The method further comprises situating the proximal end portion of the outer cannula, the proximal end portion of the inner cannula, and the bias in a housing such that a valve located in the housing is in fluid communication with the lumen of the inner cannula to allow fluid to exit a subject through the inner cannula when inserted into the subject.

In another representative embodiment, a needle assembly comprises an outer cannula defining a lumen and having a proximal end portion and a distal end portion. The distal end portion comprises a sharp bevel facilitating insertion of the needle assembly into a subject, and the proximal end portion is received in a housing. The needle assembly further comprises an inner cannula slidably disposed coaxially in the lumen of the outer cannula and movable relative to the outer cannula between an extended position and a retracted position. The inner cannula defines a respective lumen and has a blunt distal end portion and a proximal portion. The blunt distal end portion extends beyond the sharp bevel of the outer cannula whenever the inner cannula is in the extended position, and is at least partially retracted within the lumen of the outer cannula whenever the inner cannula is in the retracted position. The proximal end portion of the inner cannula is received in the housing. The needle assembly further includes a bias situated in the housing and coupled to the inner cannula and the outer cannula in a manner favoring automatic positioning of the inner cannula at the extended position unless the blunt distal end is experiencing a sufficient force to move the inner cannula to the retracted position. The needle assembly further comprises a valve located in the housing and in fluid communication with the lumen of the inner cannula and configured, when inserted into a subject, to allow fluid to exit the subject through the inner cannula. The valve is also configured to prevent ingress of fluid into the subject when a pressure inside the subject is lower than an ambient pressure. The valve includes a diaphragm configured as a one-way check valve. The needle assembly further comprises a locking assembly including a locking member defining an opening through which the inner cannula can move when the locking mechanism is activated, and an introducer port in communication with the inner cannula. The needle assembly further comprises a travel-limiting assembly including a main body and a pair of arms configured to engage slots in the housing such that the position of the main body relative to the housing can be adjusted by a user, and such that the main body can be positioned in contact with the subject. The needle assembly further comprises a visual indicator coupled to and movable with the inner cannula to indicate to a user when the sharp bevel is exposed. The foregoing and other objects, features, and advantages of the disclosed technology will become more apparent from the following detailed description, which proceeds with reference to the accompanying figures.

BRIEF DESCRIPTION OF THE DRAWINGS

FIG. 1 is a perspective view of an example of a modified Veress needle assembly according to the disclosed technology.

FIG. 2 is a detailed view of the needle assembly of FIG. 1 with an inner cannula in an extended position.

FIG. 3 is a detailed view of the needle assembly of FIG. 1 with the inner cannula in a retracted position.

FIG. 5 is a detailed side elevation view of a housing of the needle assembly of FIG. 1.

FIG. 28A is a plan view of the housing of the modified Veress needle of FIG. 9.

FIG. 28B is a cross-sectional perspective view of the housing of FIG. 28A taken along line 28B-28B of FIG. 28A.

FIG. 29A is a plan view of another embodiment of a housing including a cantilevered locking member.

FIG. 29B is a cross-sectional perspective view of the housing of FIG. 29A taken along line 29B-29B of FIG. 29A.

DETAILED DESCRIPTION

Figure 4A:
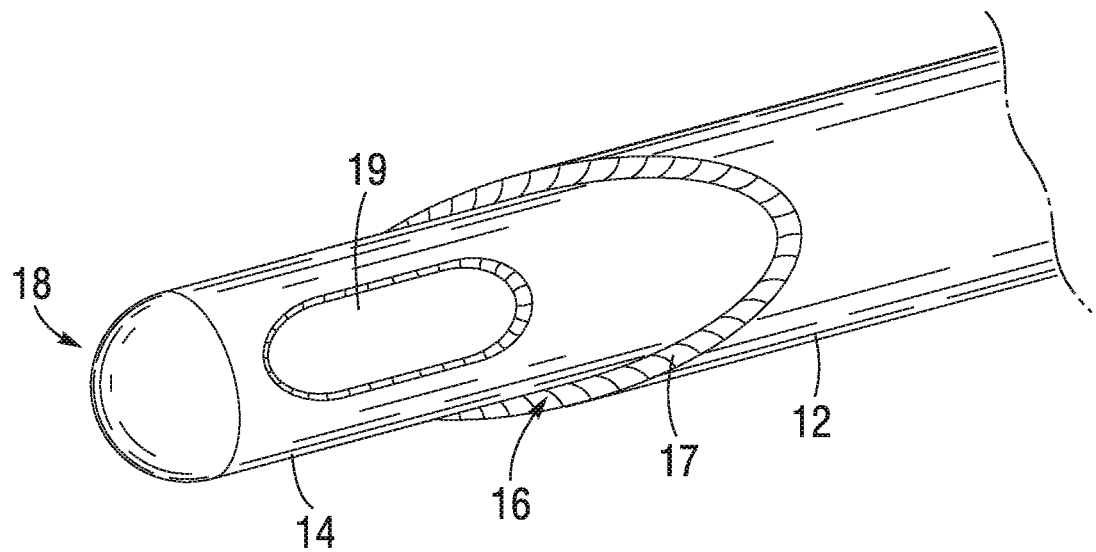
FIG. 4A is a detailed perspective view of a distal end portion of the needle assembly of FIG. 1.

Tension pneumothorax is a life-threatening condition that results from laceration to the lung and, subsequently, a parenchymal air leak. The normally sub-atmospheric pressure of the pleural space is compromised as air continues to leak into the cavity. Without a means for air to evacuate the cavity, pressure builds and impairs organ function. Treatment for tension pneumothorax (tPTX) by decompression of the pleural cavity with the use of large bore intravenous catheters is associated with a high rate of failure. In order to improve the safety and efficacy of the medical intervention, modified Veress needle assemblies/devices are disclosed for, for example, tension pneumothorax decompression. The needle assemblies were validated using swine tPTX models and demonstrated superiority to needle thoracostomy. The modified Veress needle assemblies described herein address shortcomings of other apparatus for needle thoracostomy, including: 1) inadequate needle length, 2) small bore diameter (and subsequent restricted flow rates), 3) blind sharp needle insertion, 4) lack of visual or tactile feedback, and 5) plastic sheath composition.

EXAMPLE 1

Referring to FIGS. 1-5, an example of a needle assembly configured as a modified Veress needle 10 is shown. The needle assembly 10 comprises an outer cannula 12 defining a first lumen 13 and an inner cannula 14 disposed through the first lumen 13 of the outer cannula 12. The inner cannula 14 is thereby coaxial with the outer cannula 12. The outer cannula 12 has a proximal end portion 21 and a distal end portion 23, the distal end portion 23 including a sharp bevel 16 configured, when exposed, to pierce the tissue of a body cavity of a patient when sufficient force is applied the outer cannula by a user. The inner cannula 14 defines a second lumen 15, and has a blunt distal end portion 18 including an opening 19. The opening 19 is in communication with the second lumen 15 of the inner cannula 14. The inner cannula 14 is also coupled to a bias mechanism configured, in this embodiment, as a spring 20. The inner cannula 14 is configured to move between an extended position (FIGS. 1 and 2) and a retracted position (FIGS. 3 and 5, and arrow 38 of FIG. 3) corresponding to a less-compressed state and a more-compressed state of the spring 20, respectively. Whenever the inner cannula 14 is in the retracted position, the sharp bevel 16 is in an "exposed" condition in which it can pierce tissue. Whenever the inner cannula 14 is in the extended position, the sharp bevel 16 is in an ineffective condition for piercing tissue.

The needle assembly 10 is configured such that, when the inner cannula 14 is in the extended position, the blunt distal end portion 18 protrudes beyond the sharp bevel 16 of the outer cannula 12, thereby rendering the sharp bevel 16 ineffective for piercing body tissue. However, whenever the blunt distal end portion 18 is pressed against, for example, the tissue of a body cavity, a resistance force is applied by the tissue against the blunt distal end portion 18. This resistance force can cause the spring 20 to compress. Sufficient compression of the spring 20 causes the blunt distal end portion 18 of the inner cannula 14 to travel inside the first lumen 13 of the outer cannula 12 in a retractive manner, thereby exposing the sharp bevel 16 for use in piercing body tissue. In this manner, the modified Veress needle 10 can be driven through the tissue of a body cavity by pressing the needle 10 against the tissue. Upon completing the piercing of the body cavity, the resistance pressure previously applied to the inner cannula 14 by the tissue is reduced, allowing the spring 20 to move the inner cannula 14 in the lumen 13 of the outer cannula 12 to the extended position, thereby rendering the sharp bevel 16 ineffective.

Figure 4B:
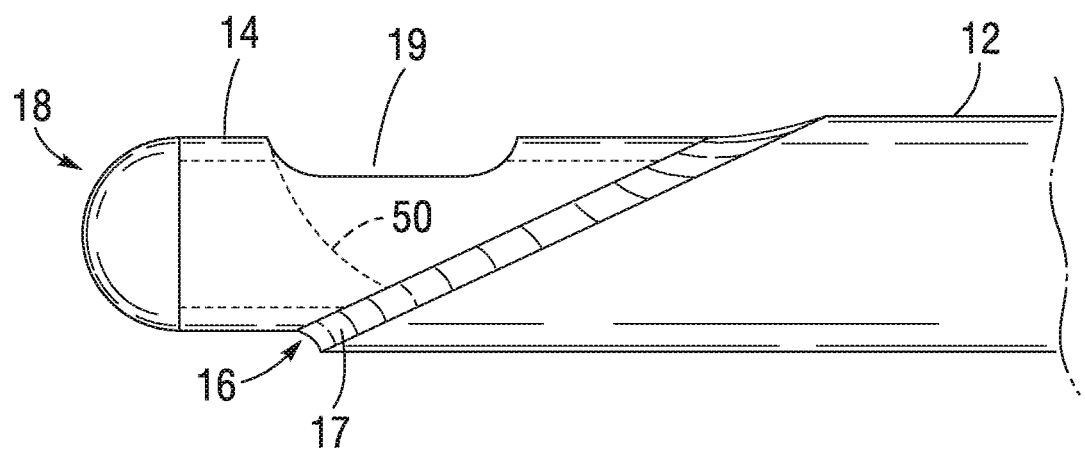
FIG. 4B is a detailed cross-sectional side-elevation view of the distal end portion of the needle assembly of FIG. 1.

Referring to FIGS. 4A and 4B, the sharp bevel 16 of the outer cannula 12 desirably is beveled such that an edge surface 17 of the bevel 16 is radiused, and curves away from the surface of the inner cannula 14 whenever the inner cannula 14 is in the extended position. The radius of the surface 17 of the sharp bevel 16 is configured such that, whenever the inner cannula 14 is in the extended position, tissue that comes in contact with the blunt distal end portion 18, or directly in contact with the sharp bevel 16, is urged along the edge surface 17 of the sharp bevel 16 without being pierced or cut by the sharp bevel 16. In this manner, the blunt distal end portion 18 of the inner cannula 14 renders the sharp bevel 16 ineffective for piercing or cutting tissue when the inner cannula 14 is in the extended position. In alternative embodiments, the edge surface 17 of the sharp bevel 16 need not be radiused, but can instead define an angle with the surface of the inner cannula 14 such that tissue is urged along the sharp bevel 16 without being cut by the sharp bevel 16, as described above.

Referring to FIG. 5, the needle assembly 10 can comprise a housing 22 having a cylindrical or frustoconical shape. The housing 22 can be coupled to the outer cannula 12 by a collar 30. The housing 22 is configured such that, when the inner cannula 14 is in the retracted position, a proximal end portion 28 of the inner cannula 14 extends from the housing 22 through an opening 34 defined in the housing 22. The proximal end portion 28 of the inner cannula 14 can comprise a color or visual pattern on its surface such that, when the inner cannula 14 is in the retracted position, the proximal end portion 28 serves as a visual indicator, indicating to a user that the sharp bevel 16 of the outer cannula 12 is exposed. Conversely, when the inner cannula 14 is in the extended position, the proximal end portion 28 is located at least partially inside the housing 22, indicating that the sharp bevel 16 is ineffective for piercing tissue. In the embodiment shown, the housing 22 is transparent, which allows a user to view inside the housing 22. In alternative embodiments, the housing 22 can be opaque, partially transparent, or can have a transparent portion, as desired.

In the depicted embodiment, the spring 20 is contained in the housing 22, and is coupled to the inner cannula 14 by a spring retainer 26. The spring retainer 26 is configured to compress the spring 20 as the inner cannula 14 is moved to the retracted position (for example, when pressure is applied to the blunt distal end portion 18), and to decompress the spring 20 accompanying motion of the inner cannula 14 to the extended position (e.g., when the applied pressure is reduced). The spring retainer 26 can be configured to move with the inner cannula 14 inside the lumen 13 of the outer cannula 12 such that, when the inner cannula 14 is in the extended position, the spring retainer 26 is located inside the lumen 13 of the outer cannula 12. Similarly, when the inner cannula 14 is in the retracted position, the spring retainer 26 is located in the housing 22 where it can serve as a visually distinguishable feature visible to a user through the transparent housing 22, as shown in FIG. 5. In this manner, the spring retainer 26 can serve as an additional visual indicator to a user that the sharp bevel 16 is exposed and the inner cannula 14 is in the retracted position.

The opening 34 defined by the housing 22 can allow a user to access the lumen 15 of the inner cannula 14 regardless of whether the inner cannula 14 is in the extended or the retracted position. Thus, the lumen 15 of the inner cannula 14 can be used as a conduit for introducing any of various instruments, such as guide wires, catheters, etc., into the body cavity pierced by the needle 10. In some embodiments, the lumen 15 of the inner cannula 14 has a diameter of about 3 mm, which can allow the modified Veress needle 10 to more effectively pass air and/or liquids from the body cavity or to the body cavity.

Figure 6:
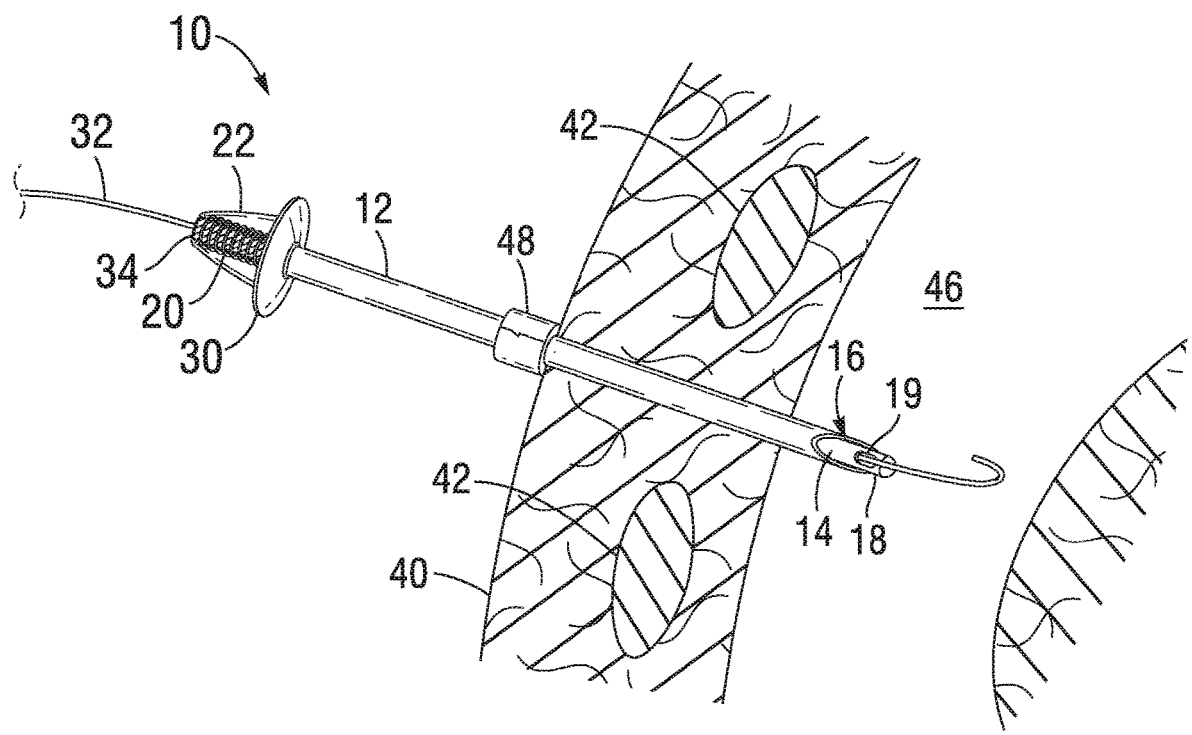
FIG. 6 is a cross-sectional side elevation view of a thoracic cavity showing an example needle assembly inserted through the thoracic wall and having a guide wire threaded through an inner cannula.
Figure 7:
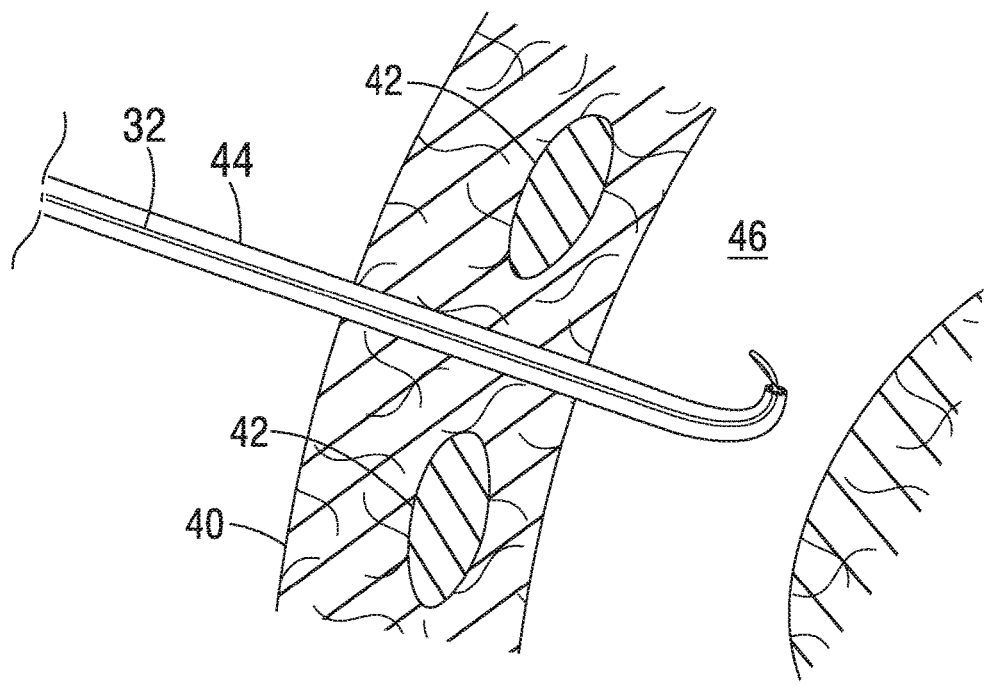
FIG. 7 is a cross-sectional side elevation view of the thoracic wall of FIG. 5 showing a pigtail catheter inserted into the thoracic cavity along the guide wire.

Referring now to FIGS. 6 and 7, the modified Veress needle 10 can be employed to treat, for example, tension pneumothorax. In an exemplary protocol, the modified Veress needle 10 is advanced through thoracic tissues into a thoracic cavity 46 by pushing the needle 10 through the thoracic wall 40 between ribs 42. As the distal end portion 18 is urged against the thoracic wall 40, the tissue of the thoracic wall 40 bears on the blunt distal end portion 18 of the inner cannula 14, thereby moving the inner cannula 14 rearwardly and compressing the spring 20. Compression of the spring 20 accompanies movement of the inner cannula 14 to the retracted position, in which the proximal end portion 28 of the inner cannula 14 extends from the housing 22 (see FIG. 5). Thus, the user is notified that the sharp bevel 16 is exposed, as described above. Upon completing the piercing of the thoracic cavity wall 40, resistance force applied to the inner cannula 14 is substantially reduced, which allows the spring 20 to decompress. This decompression of the spring 20 allows the inner cannula 14 to move to the extended position as the proximal end portion 28 correspondingly moves inside the housing 22, indicating to the user that the sharp bevel 16 is ineffective. At this time, further advancement of the needle assembly 10 into the thoracic cavity 46 can be halted, and the opening 19 in the blunt distal end portion 18 of the inner cannula 14 can be exposed. Any of various fluids such as air, blood, pus, etc., in the thoracic cavity 46, can now be withdrawn from the thoracic cavity 46 through the opening 19 into the lumen 15 of the inner cannula 14 and out of the body.

Some embodiments include a travel-limiting assembly configured as a pierce-depth limiter 48 secured to the outer cannula 12, shown configured as a flange in FIG. 6. The pierce-depth limiter 48 is attached to the outer cannula 12 at a location that prevents the needle 10 from extending too deeply into the tissue. As the modified Veress needle 10 is urged progressively further into the thoracic cavity 46, the pierce-depth limiter 48 ultimately contacts the exterior tissue of the thoracic wall 40. In such a state, the pierce-limiter 48 prevents the modified Veress needle 10 from penetrating further into the thoracic cavity 46.

Figure 8:
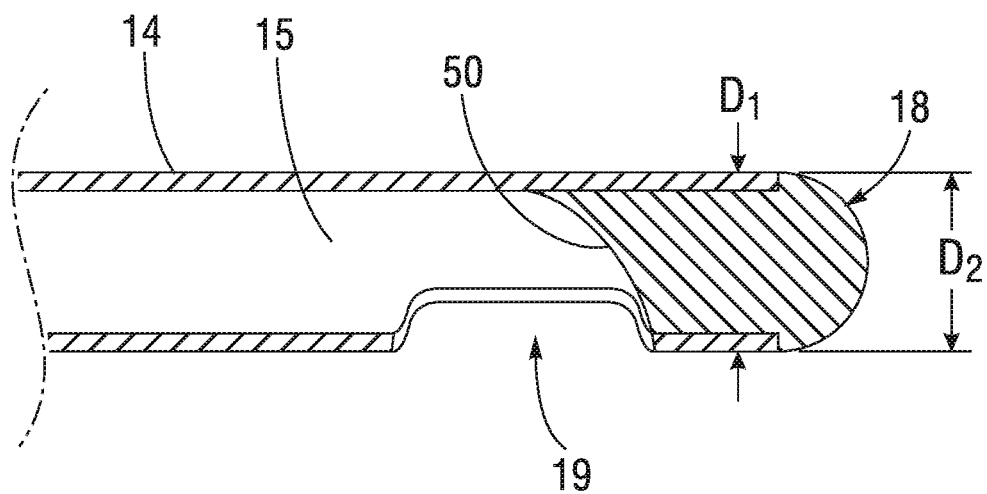
FIG. 8 is a sectional view of a distal end portion of an inner cannula illustrating a curved surface configured to guide a wire out of an opening in the inner cannula.

Still referring to FIG. 6, after the modified Veress needle 10 has been inserted into the thoracic cavity, a guide wire 32 can be inserted through the proximal end portion 28 into the lumen 15 (see FIG. 1) of the inner cannula 14. The lumen 15 defines a route through which the guide wire 32, or any other suitable instrument, can be routed into or out of the body cavity. The guide wire 32 can then be threaded through the opening 19 into the thoracic cavity 46. In some embodiments, the blunt distal end portion 18 comprises a curved interior surface 50 configured to urge the guide wire 32 through the opening 19, as shown in FIG. 8. Once the guide wire 32 has been threaded through the opening 19, the modified Veress needle 10 can be withdrawn from the tissue, leaving the guide wire 32 behind, extending through the thoracic wall 40.

The guide wire 32 facilitates insertion of any of various instruments into the thoracic cavity 46 along the guide wire 32. For example, a pigtail catheter 44, such as a SOF-FLEX® Ileal Conduit Pigtail Catheter available from Cook Medical Technologies LLC, can be threaded along the guide wire 32 into the thoracic cavity 46 for drainage or irrigation of the cavity, as shown in FIG. 7. Once the pigtail catheter 44 is in place extending through the thoracic wall 40, the guide wire 32 can be removed. Alternatively, or in addition, other instruments such as chest tubes, etc., can be introduced into the thoracic cavity 46 along the guide wire 32. The modified Veress needle 10 can also be used for performing various other procedures, including accessing the intra-abdominal cavity for laparoscopy, or for performing various percutaneous procedures, such as thoracic or intra-abdominal percutaneous drainages. In some embodiments, the needle assembly 10 can be attachable to a valve or fitting, such as a stopcock, for introduction or withdrawal of fluids to or from the thoracic cavity, respectively.

In the example depicted, the blunt distal end portion 18 is dome-shaped, by which is meant that an outer diameter $D_1$ of the inner cannula 14 is approximately equal to a diameter $D_2$ of the blunt distal end portion 18, as shown in FIG. 8. In this manner, the blunt distal end portion 18 can help to deflect tissue around the needle assembly 10 as the needle assembly 10 pierces the tissue of a body cavity. However, in alternative embodiments, the blunt distal end portion 18 can have a diameter $D_2$ that is less than the outer diameter $D_1$ of the inner cannula 14, and the edges of the inner cannula 14 can be rounded or beveled so as to urge tissue along the interface between the blunt distal end portion 18 and the inner cannula 14 without being cut or pierced. In further alternative embodiments, the blunt distal end portion 18 need not be domed, but can have any suitable shape. For example, the blunt distal end portion 18 can have a flattened configuration wherein the edges of the blunt distal end portion 18 and/or the inner cannula 14 are beveled or rounded. The blunt distal end portion 18 can also be faceted, as desired.

In some embodiments, the blunt distal end portion 18 is integrally formed with the inner cannula 14. As used herein, "integrally formed" refers to a construction that does not include any welds, fasteners, or other means for securing separately formed pieces of material to each other. In alternative embodiments, the inner cannula 14 and the blunt distal end portion 18 can be separately formed and secured together by, for example, welding, brazing, adhesive, etc.

The modified Veress needle 10 has several configurational and functional advantages compared to a conventional 14-gauge thoracostomy needle for the treatment of tension pneumothorax. The design and functional advantages of the modified Veress needle 10 include: (1) longer needle length (e.g., 14 cm modified Veress needle 10 compared to a conventional 5 cm thoracostomy needle); (2) a large bore diameter of the lumen 15 of the inner cannula 14 (e.g., 3 mm for the modified Veress needle 10 compared to 1.5 mm for a conventional thoracostomy needle); (3) tactile and visual feedback of parietal pleura penetration (e.g., using the proximal end portion 28 of the inner cannula 14 and/or the spring retainer 26); (4) the sharp bevel 16 is rendered ineffective for further tissue cutting or piercing by the blunt distal end portion 18 of the inner cannula 14 once the needle 10 is inserted in the tissue; (5) no need for use of plastic sheaths, which reduces the risk of kinking; and (6) ability to pass a wire (such as guide wire 32) through the lumen 15 of the inner cannula 14 to guide placement of a pigtail catheter.

Additional features of the modified Veress needle 10 compared to the conventional Veress needles, are: (1) a material such as masking tape placed on the inner cannula 14 can serve to limit the length of extension of the blunt distal end portion 18 out of the outer cannula 12; (2) visual indication that the sharp bevel 16 is exposed is provided by the proximal end portion 28 of the inner cannula 14; and (3) a wire can be passed from the proximal end of the inner cannula 14 and out through the opening 19 to guide, for example, pigtail catheter placement using the Seldinger technique.

EXAMPLE 2

Figure 9:
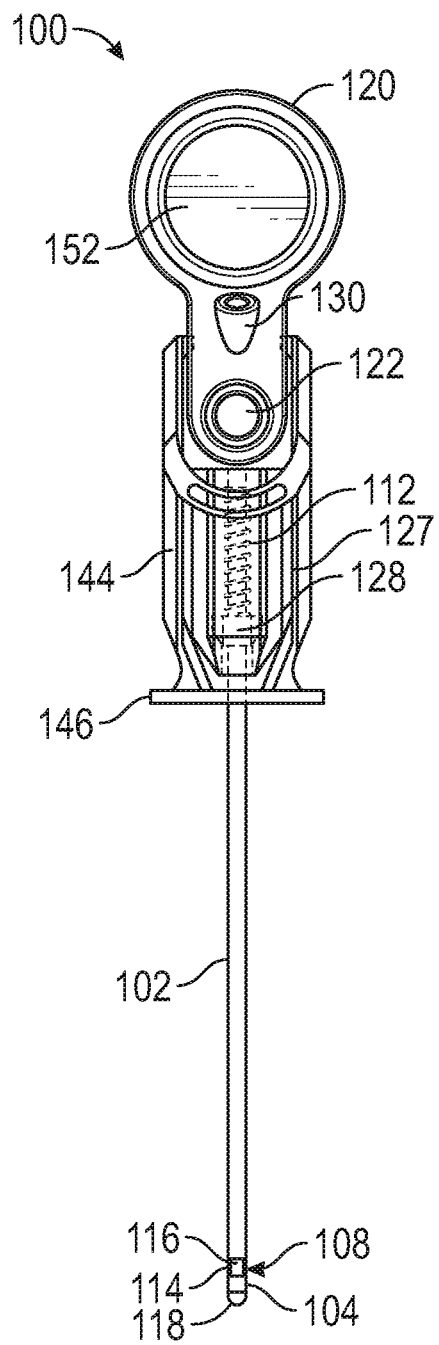
FIG. 9 is a bottom plan view of another embodiment of a modified Veress needle.
Figure 10:
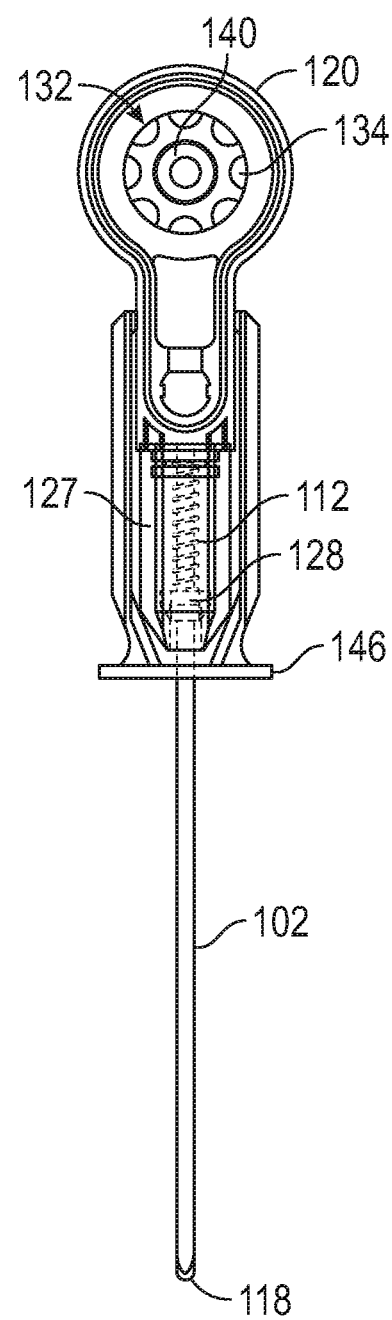
FIG. 10 is a top plan view of the modified Veress needle of FIG. 9.
Figure 11:
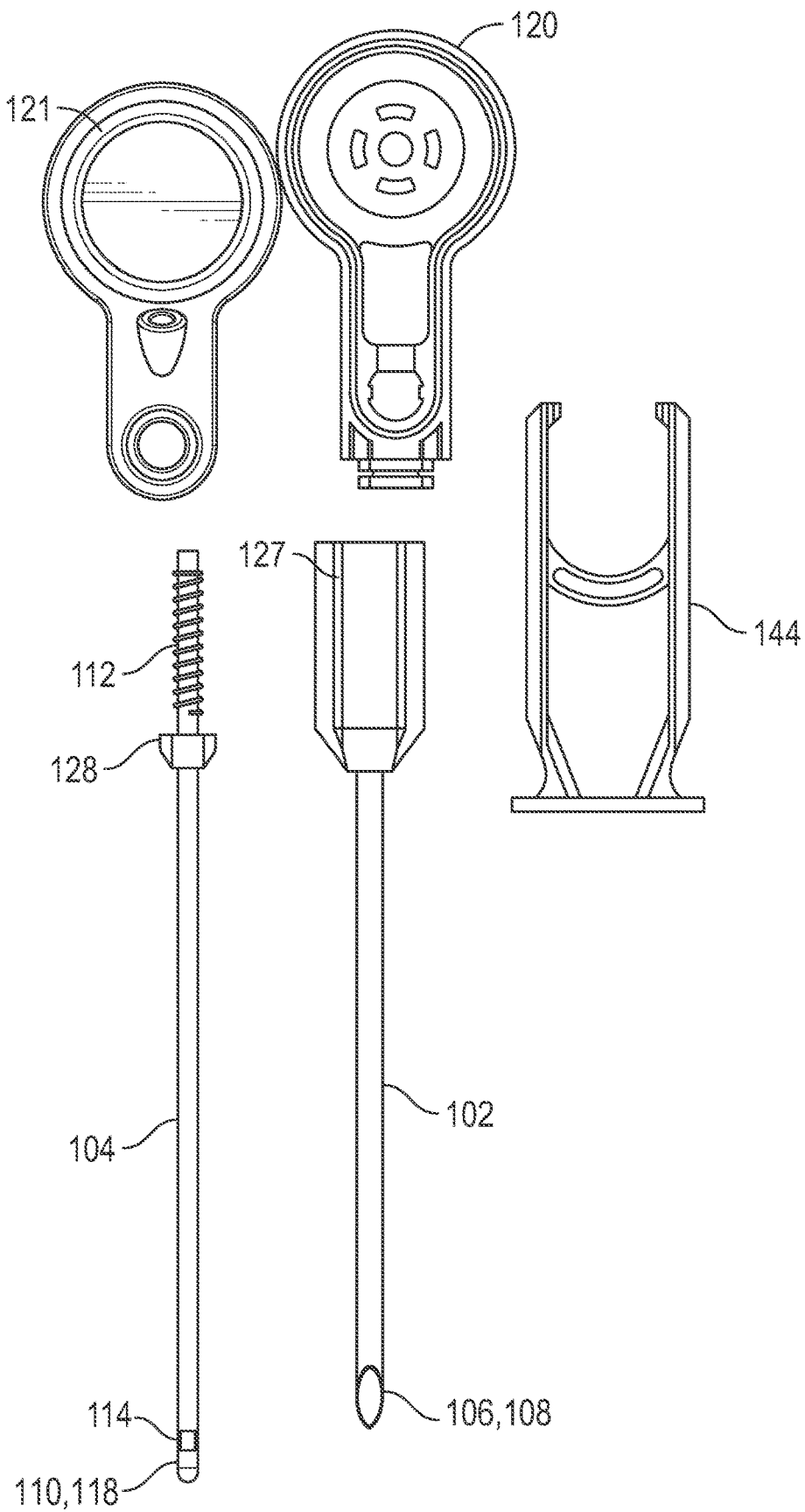
FIG. 11 is a plan view of the modified Veress needle of FIG. 9 in a partially disassembled state.
Figure 23:
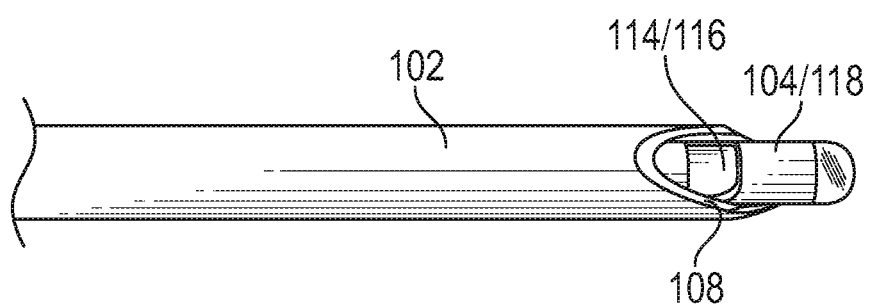
FIG. 23 is a perspective view of the distal end portion of the modified Veress needle of FIG. 9 illustrating the inner cannula in the extended position.
Figure 24:
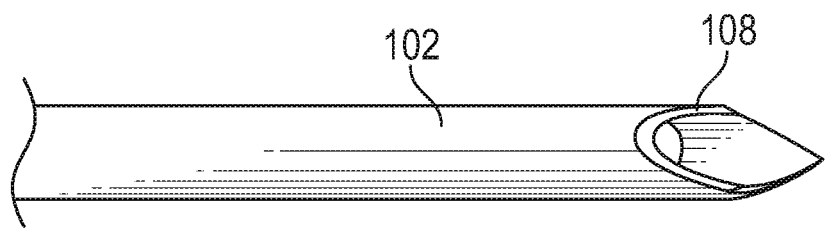
FIG. 24 is a perspective view of the distal end portion of the modified Veress needle of FIG. 9 illustrating the inner cannula retracted within the outer cannula.

FIGS. 9-34 illustrate another example of a modified Veress needle assembly 100 comprising an outer cannula 102 and an inner cannula 104 disposed through the lumen of the outer cannula 102 and movable between an extended (distal) position and a retracted (proximal) position. Referring to FIGS. 9-11, a distal end portion 106 of the outer cannula 102 includes a sharp bevel 108 configured, when exposed, to pierce the tissue of a body cavity of a patient when sufficient force is applied to the outer cannula by a user. The distal end portion 110 of the inner cannula 104 has an atraumatic tip 118 and defines an opening 114 into a lumen 116 defined by the inner cannula through which gas, liquid, etc., can exit or enter the body, as best shown in FIGS. 23 and 24. Whenever the inner cannula 104 is in the retracted position (FIG. 24), the sharp bevel 108 is in an "exposed" condition in which it can pierce tissue. Whenever the inner cannula 104 is in the extended position (FIG. 23), the sharp bevel 108 is in an ineffective condition for piercing tissue. In certain configurations, the lumen 116 of the inner cannula 104 can have a diameter of, for example, about 2 mm to about 10 mm, to promote higher flow rates than are achievable with existing pneumothorax decompression techniques and devices. In certain embodiments, the lumen of the inner cannula can have a diameter of about 3 mm.

Returning to FIGS. 9-11, the inner cannula 104 is coupled to a bias mechanism configured, in this embodiment, as a spring 112. The proximal end portions of the inner and outer cannulas can be received in a housing 120. In the illustrated configuration, the housing 120 can include an upper housing portion 121 (FIG. 12), a main housing portion 123 (FIG. 13), and a lower housing portion 125 (FIG. 14), which can be assembled together to form the housing 120. With reference to FIGS. 9-11 and 18, the spring 112 can be disposed in a spring housing portion 127, which is a respective component of the housing 120 coupled to a distal aspect of, and in fluid communication with, the housing 120. The housing 120 can also include a locking mechanism configured as a button 122 (FIG. 9) which, when pressed, allows the inner cannula 104 to move longitudinally within the outer cannula 102.

Figure 16:
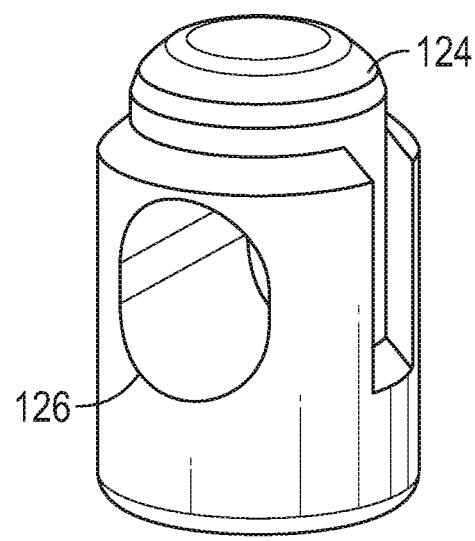
FIG. 16 is a perspective view of a locking member of the modified Veress needle of FIG. 9.
Figure 17:
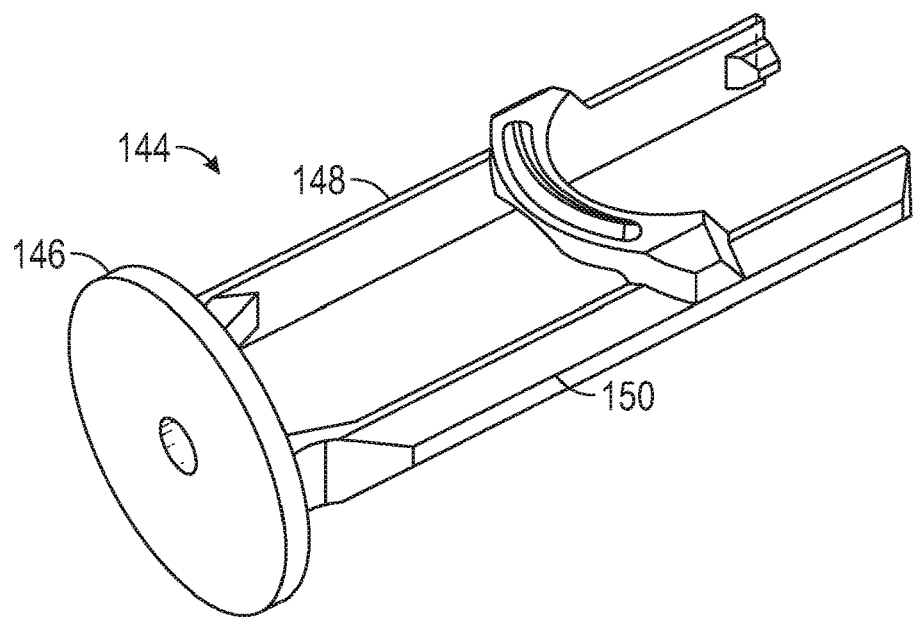
FIG. 17 is a perspective view of a representative embodiment of a travel-limiting assembly.
Figure 18:
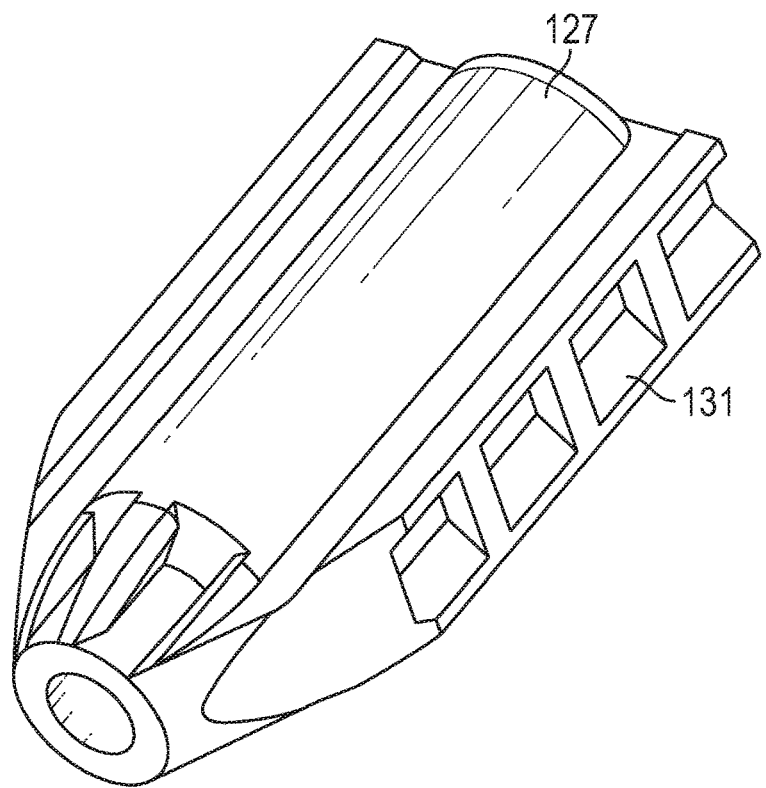
FIG. 18 is a perspective view of a representative embodiment of a spring housing portion.
Figure 19:
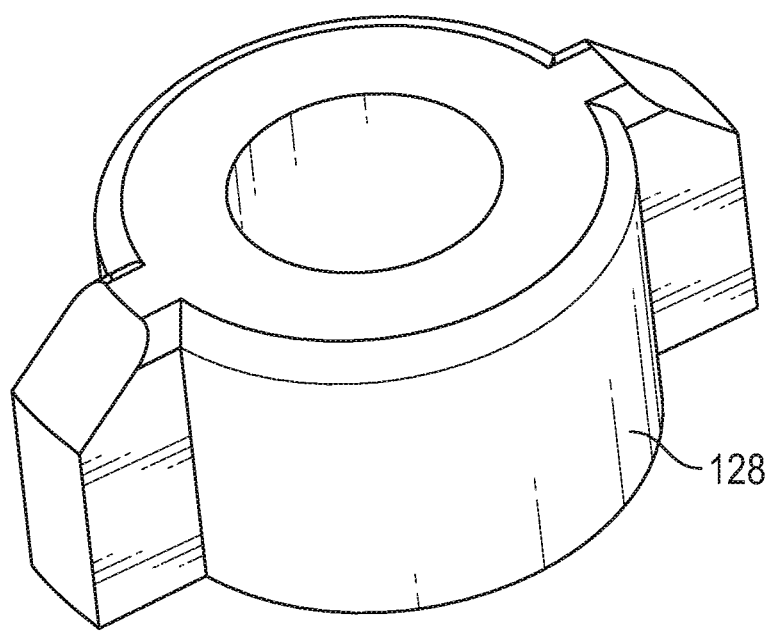
FIG. 19 is a perspective view of a visual indicator, according to one embodiment.

With reference to FIGS. 16 and 28B, a locking member 124 defining an opening 126 can be coupled to the button 122. When the button 122 is pressed, the locking member 124 can be advanced downwardly such that the opening 126 becomes coaxially aligned with the longitudinal axis of the inner cannula 104, allowing the inner cannula to move proximally through the opening 126, thereby exposing the sharp bevel 108 of the outer cannula. When the button 122 is not depressed, the locking member 124 prevents proximal movement of the inner cannula 104, thereby rendering the sharp bevel 108 ineffective. A biasing member such as a spring can bias the locking member 124 upward such that the locking member blocks proximal movement of the inner cannula. In this manner, the button 122 and the locking member 124 can prevent damage to the tissue inside the body due to inadvertent distal motion of the inner cannula.

Referring to FIGS. 9-11 and 19, the needle assembly 100 can include a visual indicator 128 coupled to the inner cannula 104 and visible through the housing 120, and more particularly through the spring housing portion 127. The visual indicator 128 can be movable with the inner cannula such that a user can determine the position of the inner cannula 104 relative to the outer cannula 102 by observing the position of the visual indicator 128. In some embodiments, the visual indicator 128 can be visible when the atraumatic tip 118 is proximally retracted to expose the sharp bevel 108, and not visible (e.g., hidden by an opaque portion of the housing) when the inner cannula is in the distal position and the sharp bevel is ineffective.

Figure 12:
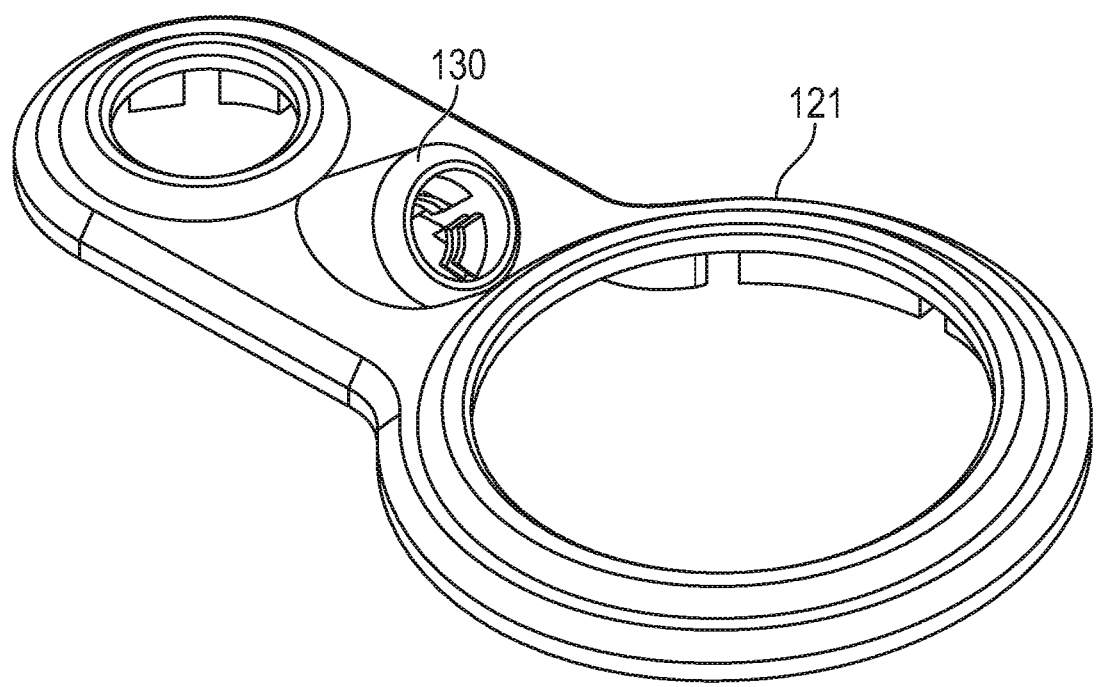
FIG. 12 is a perspective view of an upper housing portion of the modified Veress needle of FIG. 9.
Figure 13:
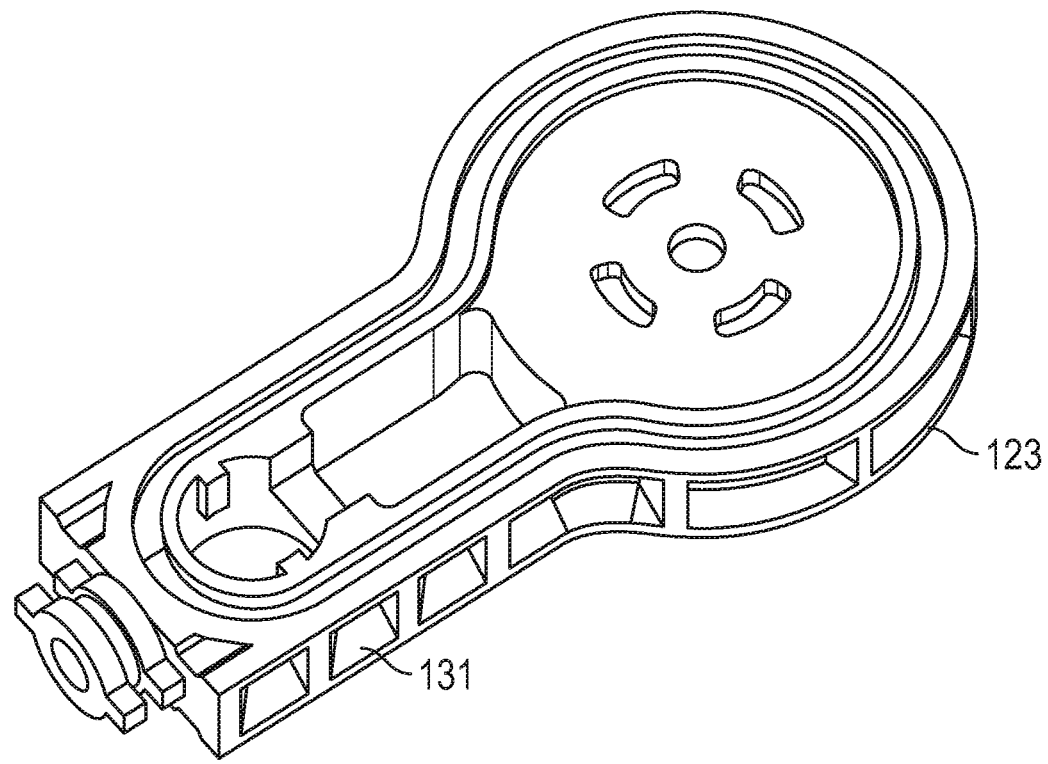
FIG. 13 is a perspective view of a main housing portion of the modified Veress needle of FIG. 9.
Figure 20:
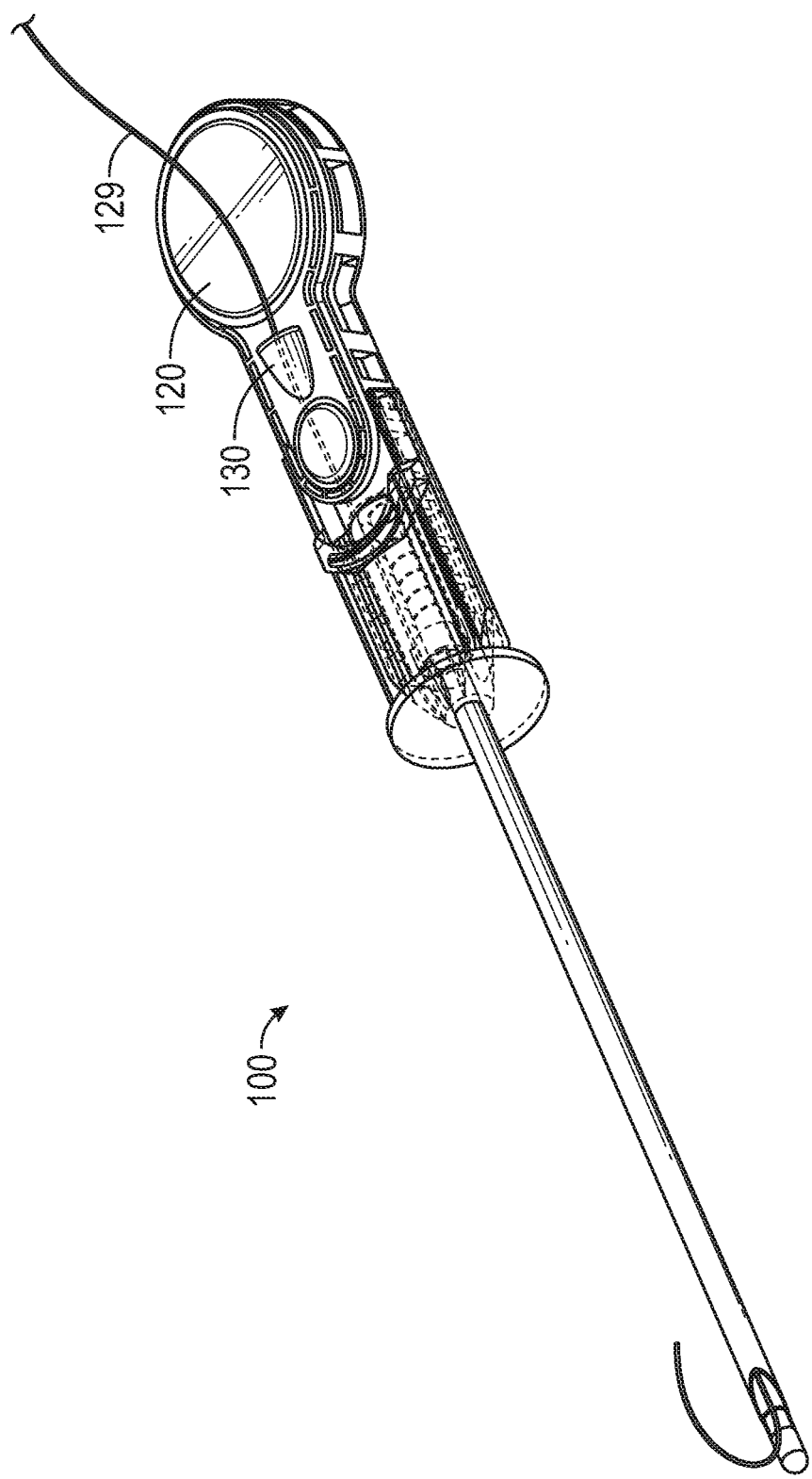
FIG. 20 is a perspective view of the modified Veress needle of FIG. 9 illustrating a guide wire extending through a port in the housing and through an opening at the distal end of the inner cannula.

With reference to FIGS. 9 and 12, the housing 120 can also include an introducer port 130 in communication with the lumen 116 of the inner catheter 104 and through which items, such as a guide wire 129, may be inserted (see FIG. 20). In some embodiments, the introducer port 130 can include a sealing material extending across the opening of the port and intended to seal around objects inserted into the port to prevent, for example, ingress of unwanted gas, liquid, etc., into the body. The guide wire 129 may be used to place a chest tube or catheter, such as a pigtail catheter.

Figure 14:
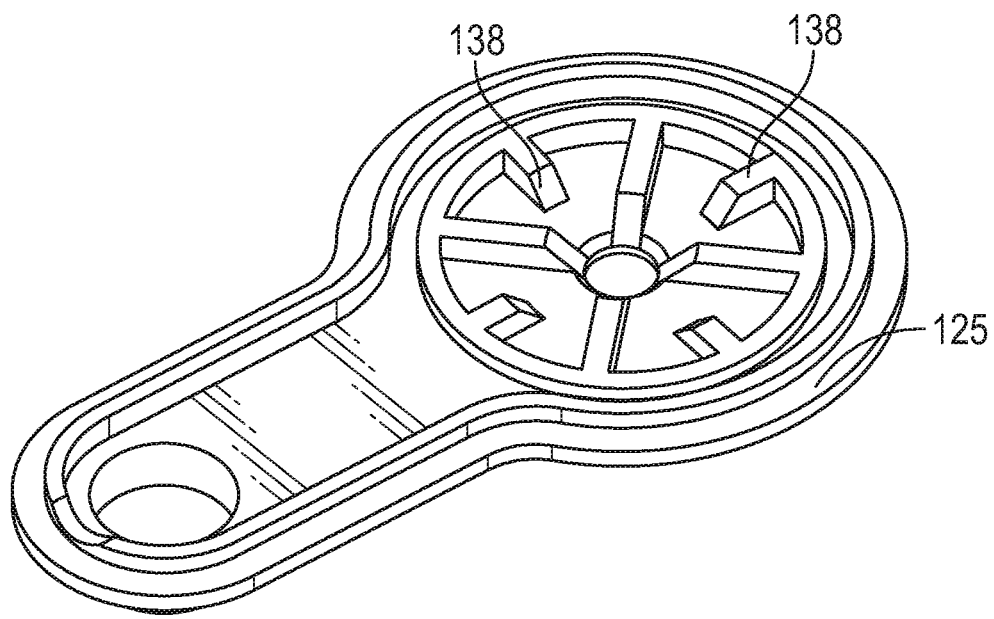
FIG. 14 is a perspective view of a lower housing portion of the modified Veress needle of FIG. 9.
Figure 15:
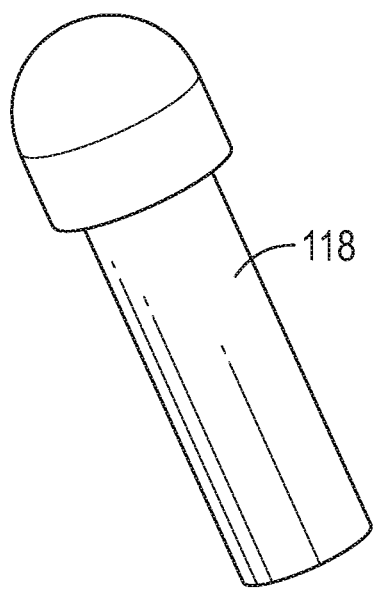
FIG. 15 is a perspective view of an exemplary embodiment of an atraumatic tip that can be used with the modified Veress needle of FIG. 9.
Figure 21:
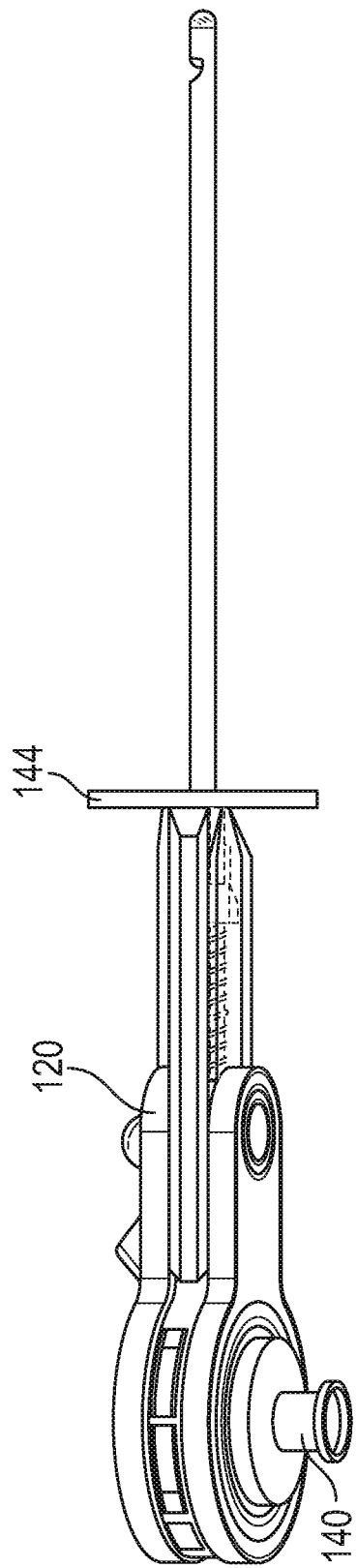
FIG. 21 is a side view of the modified Veress needle of FIG. 9 showing a Luer lock.
Figure 22:
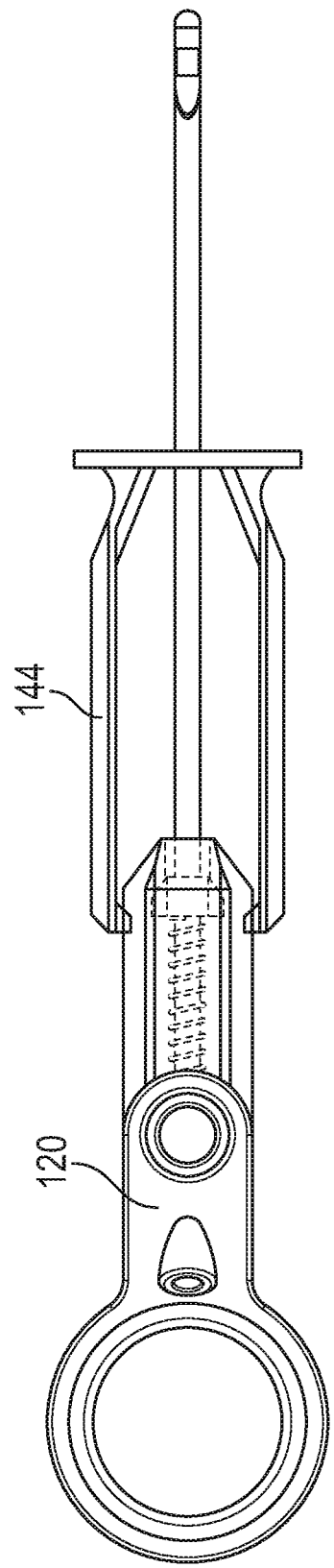
FIG. 22 is a top plan of view the modified Veress needle of FIG. 9 with the main body of a travel limiting assembly in the extended position.

Referring again to FIG. 10, the needle assembly 100 can also include a valve assembly 132 configured as a check valve. As shown in FIGS. 10, 14, 25, 28 the valve assembly 132 can include a flexible flap seal or diaphragm 134 (FIG. 25) disposed in a chamber 136 (FIG. 28B) defined in the housing 120 and supported by one or more support members 138 (FIGS. 14 and 28B). In this manner, the valve assembly 132 can allow the evacuation of excess pressure from the body (e.g., in a condition of tension pneumothorax), and prevent the ingress of gas or liquid into the body through the needle assembly if pressure in the body returns below ambient (e.g., atmospheric) pressure. With reference to FIGS. 10 and 21, the housing 120 can also include a fitting or port configured as a Luer lock port 140 (e.g., a male Luer lock port) by which the needle assembly can be coupled to other elements, such as a drainage bag. In this manner, fluids can be drained from the body and collected without the need to insert a chest tube. The lock port 140 can also be configured for connection to other devices, such as a stopcock, a fluid source, etc. In some embodiments, the diaphragm 134 can be configured to vibrate when fluid passes through the valve to provide tactile feedback to the user.

Figure 25:
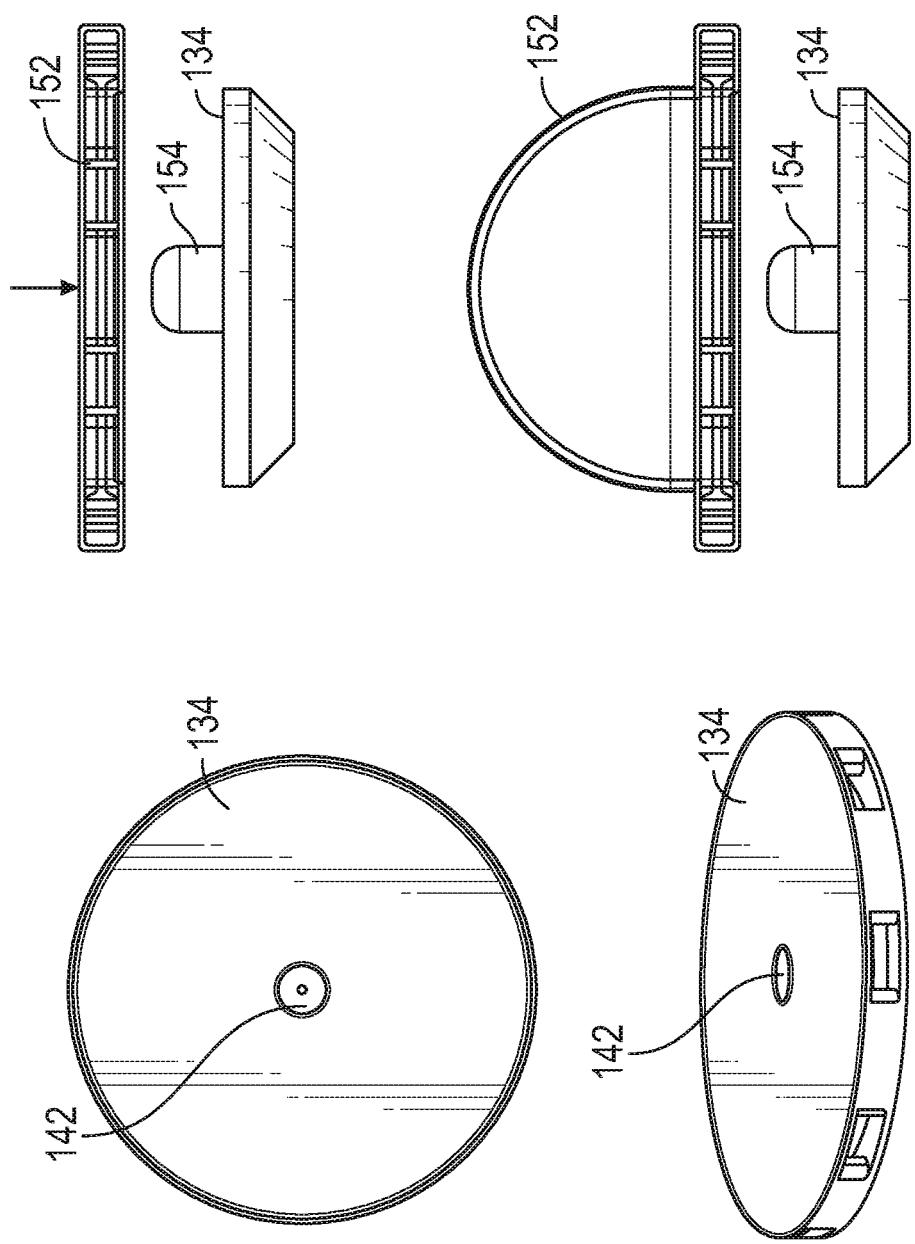
FIG. 25 illustrates various views of a diaphragm, according to one embodiment.

Referring to FIG. 25, the diaphragm 134 can include an indicator 142. In the illustrated configuration, the indicator 142 is positioned at the center of the diaphragm, and is configured to expand or inflate when under the influence of gas or liquid exiting the body through the needle assembly. In this manner, the indicator 142 can approach or contact the housing 120, providing a visual indication to the user that gas or liquid is flowing through the needle assembly. In some configurations, the indicator 142 can be colored, such that its interaction with the housing 120 causes the indicator to appear to change colors when viewed by the user. In another embodiment illustrated in FIG. 25, the housing can include a flexible membrane 152 configured to expand or inflate when fluid flows through the valve 132, which can indicate to a user that fluid under positive pressure is flowing out of the body through the valve. In some embodiments, the diaphragm 134 can include a protuberance 154 on which the flexible membrane 152 can rest when not inflated, such that the protuberance is visible through the flexible material to the user (see also FIG. 9).

Referring to FIGS. 17, 21, 22, and 30, the needle assembly can include a travel limiting assembly 144 including a main body 146 having two arms 148, 150 and movable between an extended position (FIG. 22) and a retracted position (FIG. 21). In the illustrated configuration, the outer cannula 102 can extend through an opening 172 (FIG. 30) defined in the main body 146. The arms 148, 150 can be configured to engage slots 131 in side portions of the housing 120 and/or of the spring housing portion 127 (see FIG. 18), such that the position of the main body 146 relative to the housing can be selected by the user. In use, when the needle assembly 100 has been inserted to a specified depth in the body, the travel limiting assembly can be moved to the extended position such that the main body 146 contacts the patient, thereby preventing further distal motion of the needle assembly into the body cavity. In certain configurations, the surface of the main body 146 can include an adhesive configured to adhere to the skin of the patient and prevent movement of the needle assembly after insertion to a specified depth.

Figure 26:
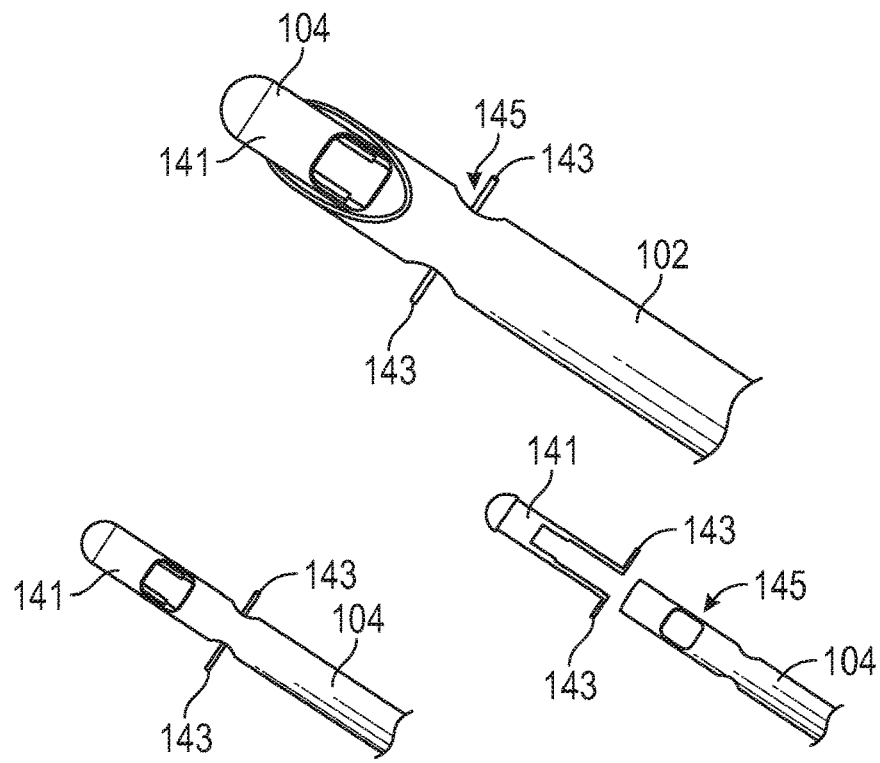
FIG. 26 illustrates another embodiment of a modified Veress needle including a atraumatic tip having barbs.

In certain configurations, the modified Veress needle 100 can include one or more retention features configured to engage surrounding tissue and keep the needle at a selected depth in a body cavity in which the needle is inserted. For example, FIG. 26 illustrates an embodiment in which the inner cannula 104 includes a separable atraumatic tip portion 141 including two extension portions configured as barbs 143 that extend through corresponding openings 145 in the outer cannula 102. The barbs 143 can be configured to anchor the modified Veress needle in surrounding tissue. In certain embodiments, the barbs may be maintained in a retracted state by the walls of the outer cannula 102, and may be deployed by rotating the outer cannula such that the openings 145 become aligned with the barbs 143, allowing the barbs to extend outwardly to engage surrounding tissue.

Figure 27:
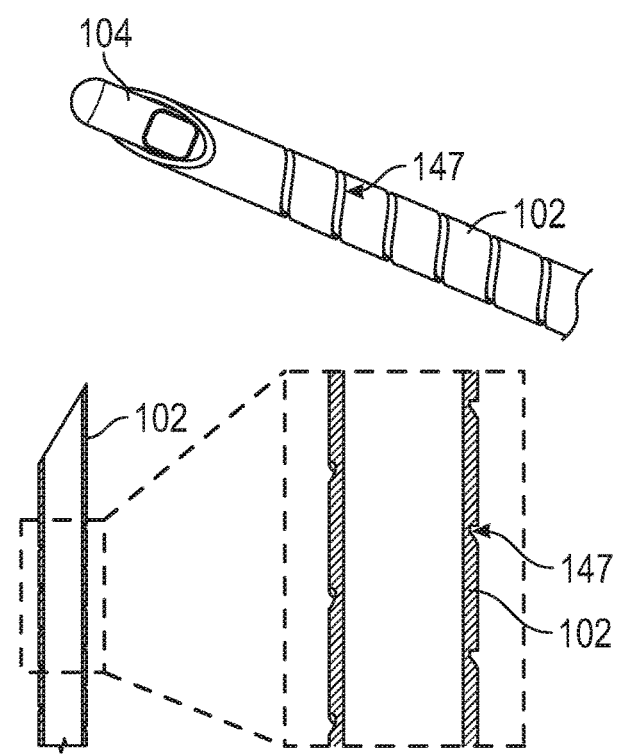
FIG. 27 illustrates another embodiment of a modified Veress needle wherein the outer cannula includes a spiral-shaped groove.

FIG. 27 illustrates another embodiment in which the outer cannula 102 includes a retention feature configured as a groove 147 extending in a spiral shape along at least a portion of the length of the outer cannula. The groove 147 can be configured to engage surrounding tissue to hold the modified Veress needle in place at a selected depth in a body cavity. In other embodiments, the outer cannula 102 can include various other surface texture features, such as bumps, barbs, etc.

FIGS. 29A and 29B illustrate another embodiment of the housing 120 in which the housing includes an integral locking member 133 that extends in a cantilevered fashion into an opening 135 defined in the housing. The locking member 133 can have a blocking portion 137 that is aligned with a lumen 139 in which the inner and outer cannulas are received, and which is configured to block or prevent proximal motion of the inner cannula 104 when the locking member is in its normal, non-deflected state. When the locking member 133 is downwardly depressed, the blocking portion 137 can move below the lumen 139, allowing proximal motion of the inner cannula.

Figure 31:
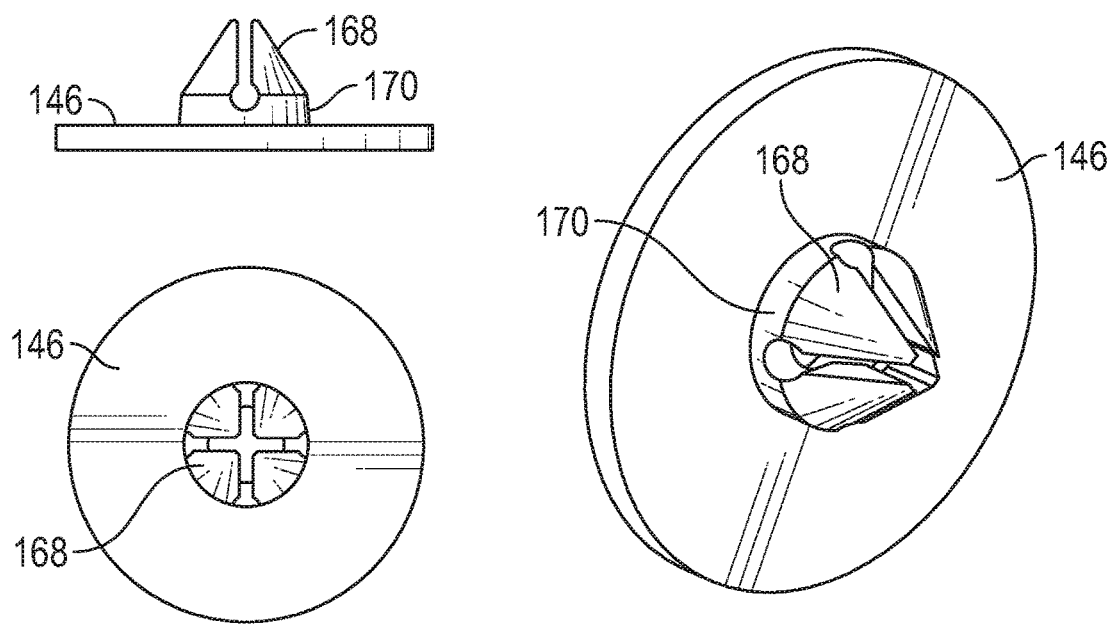
FIG. 31 illustrates another embodiment of a main body of a travel-limiting assembly.

FIG. 31 illustrates another embodiment of the main body 146 of the travel-limiting assembly 144 including four movable tab portions 168. The tab portions 168 can frictionally engage the outer cannula 102 to resist movement of the main body relative to the outer cannula. When the main body 146 is moved distally (e.g., toward the patient's body), the tab portions 168 can be deflected radially outward, reducing the friction between the tab portions and the outer cannula, and allowing the main body to move distally. In the illustrated embodiment, the tab portions 168 extend from a cylindrical collar portion 170, although other configurations are possible. When the main body 146 is moved proximally (e.g., away from the patient's body), the tab portions 168 can be deflected radially inwardly such that the frictional engagement between the tab portions and the outer cannula increases. This can help to prevent inadvertent proximal motion of the main body 146 relative to the outer cannula 102 (or vice versa), helping to keep the main body in a selected position once placed in contact with the user's body. In alternative embodiments, the main body 146 can include any suitable number of tab portions, such as two tab portions, three tab portions, etc. Additionally, although the tab portions 168 in the illustrated embodiment have triangular shape, it should be understood that the tab portions can have any suitable shape, such as a square shape, a rounded shape, etc., depending upon the particular characteristics desired.

Figure 32:
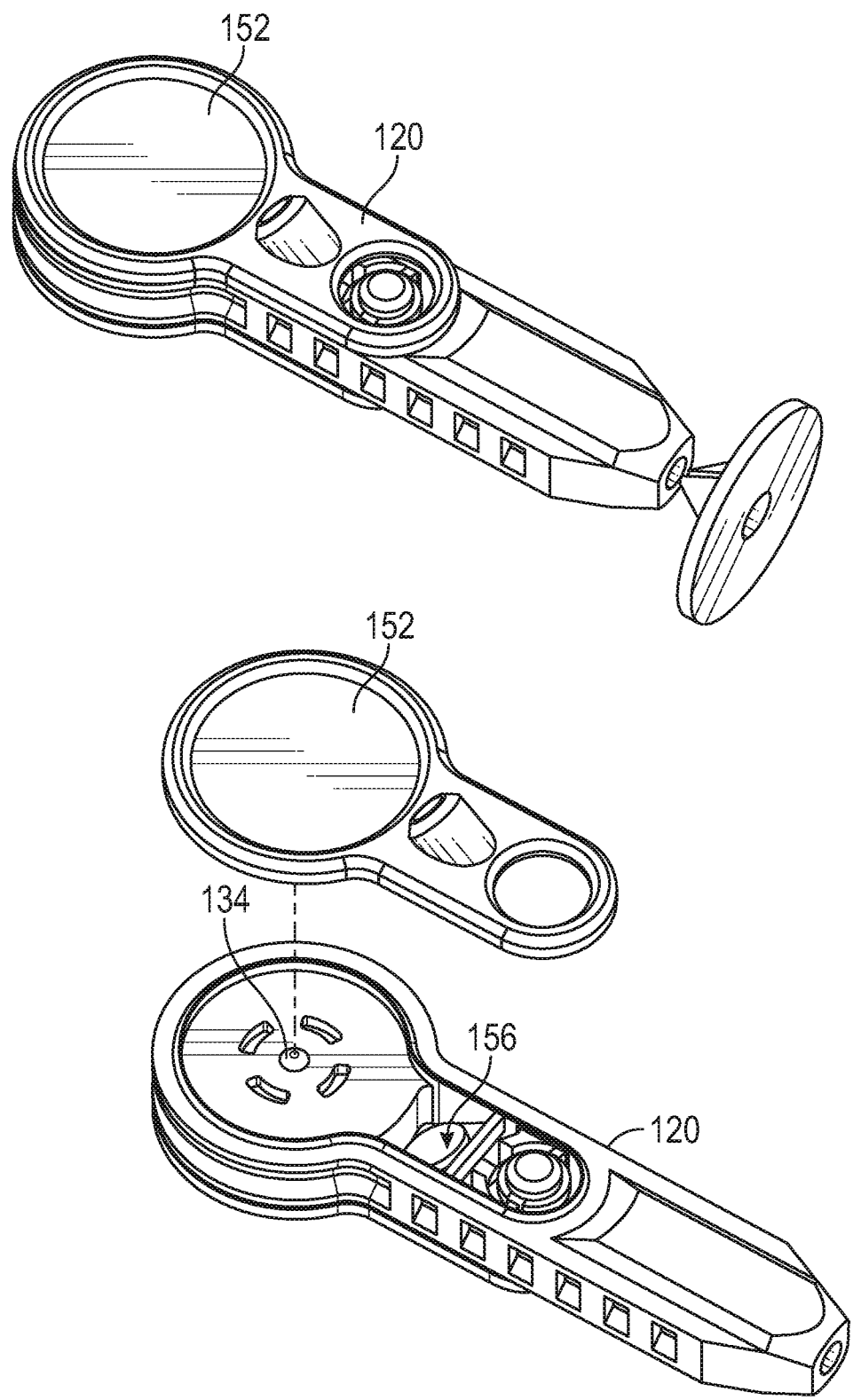
FIG. 32 illustrates perspective views of another embodiment of a housing including a one-way valve.

FIG. 32 illustrates another embodiment in which the needle assembly includes a second valve assembly 156 located downstream of and in fluid communication with the diaphragm 134 and the flexible membrane 152. In some configurations, the valve assembly 156 can be a one-way check valve that can allow the flexible membrane 152 to be used as a manual pump. For example, in some configurations, compression of the flexible membrane 152 by a user when the membrane is in the expanded configuration can cause the diaphragm 134 to seal against the support members 138, cause the valve assembly 156 to open, and force fluid out of the needle assembly through the valve assembly 156. When the flexible membrane 152 is released, the valve assembly 156 can close. If the flexible membrane 152 is compressed beyond its normal non-deflected position (e.g., the position of the flexible membrane 152 when the pressure on both sides of the diaphragm 134 is substantially equal), the flexible membrane can return to its non-deflected position when released by the user. This can reduce the pressure on the inflow side of the diaphragm 134, causing the diaphragm 134 to open and drawing fluid out of the pleural cavity, through the inner cannula, and into the needle assembly. The flow of fluid through the diaphragm 134 can cause the flexible member 152 to return at least to its non-deflected state, and the flexible membrane 152 can then be compressed again to force the fluid out of the needle assembly through the valve assembly 156. In this manner, the flexible membrane 152 can function as a pump to remove fluid from a body cavity in, for example, emergency situations where other pumping devices (e.g., in-line hand pumps) are unavailable.

Figure 33:
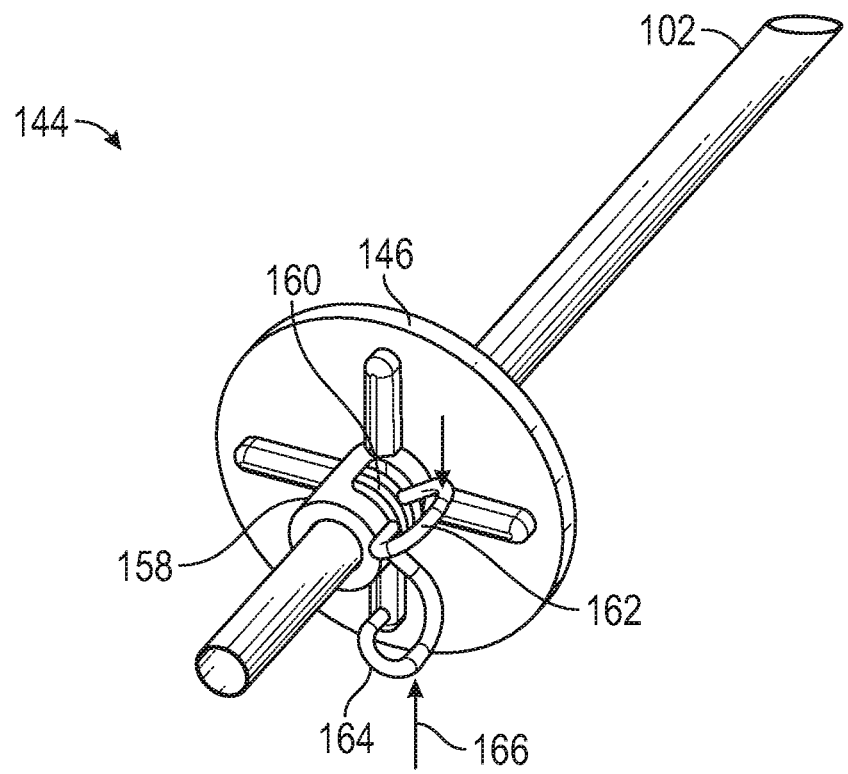
FIG. 33 is a perspective view illustrating another embodiment of a travel-limiting assembly including a collar disposed around the outer cannula.
Figure 34:
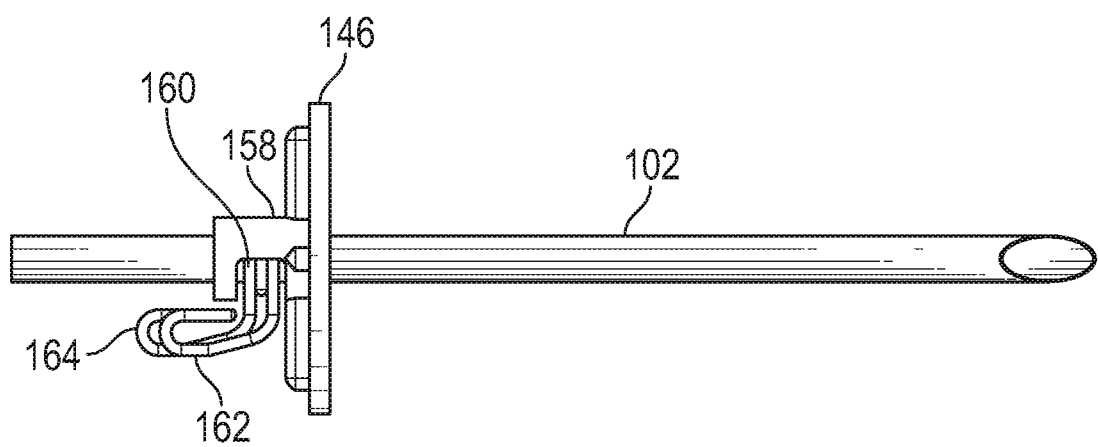
FIG. 34 is a plan view of the travel-limiting assembly of FIG. 33.

FIGS. 33 and 34 illustrate another embodiment of the travel-limiting assembly 144 in which the main body 146 includes a collar portion 158 disposed around the outer cannula 102. A coiled spring configured as a spring collar 160 is disposed about the outer cannula 102 within the collar portion 158. The spring collar 160 can include two arms 162, 164 extending from the collar portion 158 and movable between a first position (FIG. 33) and a second position. When the arms 162, 164 are in the first position, the spring collar is in a non-deflected state and has a first radius configured such that the spring collar frictionally engages the outer cannula 102. When the arms 162, 164 are pressed toward one another in the manner of arrows 166 (e.g., to the second position), the movement of the arms can increase the radius of the spring collar 160 so that the spring collar no longer engages the outer cannula 102, allowing the travel-limiting assembly 144 to be moved longitudinally along the outer cannula. When the arms 162, 164 are released, the spring collar 160 can contract back to its non-deflected state to frictionally engage the outer cannula. In this manner, the position of the main body 146 along the outer cannula can be easily adjusted by a user.

Features of the Modified Veress Needle Assembly 100

A number of features are exhibited in the example modified Veress needle assembly 100, which can be used alone or in combination and/or subcombination with each other, and with any of the needle assembly embodiments described herein. In some examples of the disclosed technology, a manual locking mechanism is integrated into the device to secure the internal cannula in the deployed state and protect viscera from the sharp needle tip during handling.

In some examples, a one-way valve is integrated into the device 100 so that atmospheric pressure does not compromise organ function with the vented pleural cavity.

In some examples, a flow indicator is integrated into the needle assembly 100 so operators are able to monitor decompression and sustained device functionality.

In some examples, design elements are integrated into the needle assembly 100 in such a fashion as to improve compatibility with available medical kits (drainage bags, catheters, etc.).

In some examples, a deployable anchor is integrated into the sheath of the syringe assembly that can help to prevent device from unintentionally dislodging from the pleural cavity (prevents egress).

In some examples, an adjustable flange can be integrated into the needle assembly 100 that interfaces with patient's chest to reduce or prevent further penetration into the pleural cavity (prevents ingress).

In some examples, a visual indicator can be incorporated into the needle assembly 100 for a user to monitor internal cannula position (extended or retracted).

In some examples, the modified Veress needle 100 can include an augment flow indicator.

In some examples, the modified Veress needle 100 can include a guidewire port.

Suitable modified Veress needle and tPTX device designs for optimal interface. In should be understood to one of ordinary skill in the relevant art that any combination of these features can be used together with any of the modified Veress needle embodiments described herein.

Example Experimental Results

Aspect 1: Locking Mechanism

The locking mechanism including the locking member 124 can secure the spring-loaded, internal cannula of the modified Veress needle in place after successful penetration of the pleural cavity. This can help to protect delicate tissue from the sharp needle during handling and decompression. The locking mechanism may be easily engaged/disengaged during manual operation but secure so that inadvertent engagement/disengagement is unlikely. Additionally, the method of engaging/disengaging the lock can be ergonomic and promote stable handling. Furthermore, the mechanism can be simple so that it is easily manufactured and less susceptible to variability.

Functionality and usability/ergonomics were tested to assess locking mechanism design. Functionality was assessed based on lock stability under increasing, static compressive loads; lock stability after 100 cycles (engage/disengage); and lock stability after drop testing (3 ft. unweighted, 3 in. weighted to simulate stress and strain rates that may be seen with an inadvertent "bump"). Ergonomics was tested during a user evaluation where subjects are instructed on how to use the device and then follow a protocol for simulated use and puncture of a septum.

Locking mechanisms for the first specific aim were evaluated for stability under compressive loads, fatigue resistance during cycling of the locking mechanism, impact resistance for 3 ft. drops, and ergonomics. In a representative embodiment, the functional prototype locking mechanism withstands compressive loads in excess of 20 lbs, repetitive use over 100 cycles, 3 ft. drops onto hard surfaces, and weighted impacts akin to inadvertent bumps against hard surfaces. Ergonomics of the locking mechanism were evaluated and found suitable for the application. The design incorporates a cantilever-style obstruction that braces against the interior cannula of the modified Veress needle which is depressed via a button during insertion. This allows the cannula to retract, exposing the needle. Once the pleural cavity is reached, the spring loaded cannula snaps back into place and the operator releases the button thereby securing it in place.

Aspect 2: One-Way Valve

There are numerous styles of one-way valves that may be implemented in this design. In some example configurations, (e.g., having high flow rates of ~13 L/min, low operational pressures of 5 mmHg, and kit compatibility), elastomeric/diaphragm style valves can be suitable for the application. A one-way valve may also be made using a spring-loaded piston. Both elastomer/diaphragm and spring-based valve systems are being designed with 4 alternative configurations for each. Four alternative configurations for the elastomer/diaphragm based system include: 1) a flapper style diaphragm; 2) leaflet/flap diaphragm; 3) bi- or tri-leaflet diaphragms; and 4) a compression diaphragm. The four alternative configurations for the spring-based system include: 1) a torsion-spring based flap; 2) a spring-loaded piston; 3) a torsion-spring based flap with unique geometry; and 4) a spring-loaded piston with unique geometry. The geometries are relevant because they involved varying seal compression (static and dynamic seals differ in recommended gasket compression for different applications), seal surface area (necessary to achieve desired forces at given pressures), and the degree of flow obstruction (necessary to trigger indicators).

Valve designs were evaluated to assess cracking pressure, minimal flow pressure, permissible flow rates, and reverse-flow pressure limits (how much pressure is required for the one-way valve to fail). Cracking pressure, minimal flow pressure, and failure pressures were determined by connecting the valves to increasing hydrostatic pressures determined by pressure heads created using differential fluid column heights. Cracking pressure is established when a hydrostatic pressure results in flow through the valve. Minimal flow pressure is calculated based on the height of the fluid column remaining after flow through the valve ceases. The pressure limit may be established in a similar fashion by reversing the connection of the fluid column to the valve. Higher pressures may be achieved for either test setup by using a syringe and attempting to force fluid through the valve. Flow rates may be determined by connecting the valve in line with a peristaltic pump and fluid reservoir in a closed loop and increasing flow rates until failure. It should be noted that water can be suitable for conducting these tests as the only major difference (for these purposes) is that air is compressible and water is not; cracking pressure and flow rates may be similar. Valves will also be tested using air to ensure the seals are gas-tight.

One-way valves for the second specific aim were evaluated for crack pressure, minimal flow pressure, permissible flow rates, and back-flow resistance. The design for the functional prototype one-way valve exhibits an adjustable crack pressure that may be set as low as 2-3 mmHg, minimal flow pressures below the crack pressure (less than 2 mmHg), permissible flow rates within 10-15% of the modified Veress needle (without any flow impediments), and resistance to back-flow when exposed to increasing pressures up to or beyond 80 mmHg. The design incorporates an umbrella valve made of soft silicone that creates a contact seal within the device. Flow may only proceed in a singular direction unless the valve is compromised.

Aspect 3: Flow Indicator

Four options for flow indicators were evaluated. These include 1) a fluid reservoir, 2) a hinged flow obstruction, 3) in-line turbine/wheel, or 4) piston arm. The options can be selected for a particular implementation depending on a specified application. For example, the fluid reservoir is the simplest design that indicates flow as bubbles pass through the reservoir. The reservoir can also indicate the flow of other fluids as the fluid level will rise within the reservoir attached to a drainage bag.

Indicator evaluation can include two styles of testing: functionality and accuracy. With functional testing, the indicators designs would be assessed in a blind study where a subject is instructed on what to look for and to note when there is and isn't flow. It is possible to associate flow rates within a range of indicator responses (beyond a YES/NO indication). For example, the water reservoir can be a suitable YES/NO indicator and/or flow rate indicator. The turbine/wheel style indicator can be attached to a "clicker" that provides audible feedback. The frequency of clicks may then be attributed to specific flow rates. All four designs can be tested and tuned using both water and air.

Flow indicators for the third aspect aim were evaluated under high/low flow conditions, high/low pressure conditions, and using both fluid and gas. The design for the functional prototype flow indicator operates under both high/low flow and pressure conditions using both liquid and gas. Furthermore, the flow indicator notifies the operator if flow is compromised (and pressure builds within the pleural cavity) or if normal physiologic conditions are restored (and a negative pressure within the pleural cavity is achieved). The design incorporates a displacement style flow indicator made of a silicone diaphragm which deforms into a concave or convex configuration depending on the internal pressure of the device.

Aspect 4: Kit Compatibility

Certain examples can be designed in a modular fashion so that alternative designs from each category are interchangeable and may be assembled to produce a final design with optimal performance characteristics. Given the modular nature, snap-fittings or luer lock fittings will be attached at the outlet so the device may be readily connected to other medical kits (such as drainage bags). For compatibility with catheters, diaphragm designs are the most acceptable, as the plunger style one-way valve would typically require additional parts or tubing to circumnavigate the flow obstruction.

The compatibility of the device with other medical kits was tested. It is often desirable that the adapters be designed into the device to securely attach and interface with the components of the other kits (luer-lock fittings, snap-fittings, barbed fittings, etc.). Also, in certain embodiments, a catheter guidewire can pass through the device without becoming entangled.

Compatibility with other medical kits or components can be achieved by combining the aforementioned designs into a single device comprising four parts and luer lock fittings at the inlet and outlet of the tPTX device. In addition, the inlet and outlet of the device are designed to be easily modified without compromising the performance characteristics of the device. As a result, these ports may be adjusted depending on the application to include barbed fittings for tubing, quick connect/disconnect fittings, or permanent mounts.

Aspect 5: Anchor

Examples of disclosed anchors can prevent the device from dislodging from the pleural cavity or becoming obstructed while in use. The hypodermic syringe can include slots to align with collapsible obstructions that deploy after insertion of the needle assembly into the pleural cavity. The obstructions can be made of, for example, a biocompatible polymer. The obstructions can be soft to prevent tissue damage and contoured to prevent pull-out.

The anchor mechanism was evaluated for pull-out resistance, ergonomics, and fatigue failure. Pull-out resistance was tested by deploying the device in a simulated chest wall (made of silicone elastomer and urethane plastic) and applying an incremental tensile load until failure. In some embodiments, a tensile load of 20 lbs is an approximate goal for pull-out resistance. Ergonomics can be adjusted for comfort and operational simplicity. Fatigue failure was assessed by cycling the anchor mechanism 100 times and monitoring the device for mechanical failure. The device may be repositionable so that the anchor is easily deployed and retracted multiple times without failure.

Two styles of anchor designs were created for the project and testing. These designs included textured hypodermic syringe and barbed hypodermic syringe assemblies. The textured hypodermic syringe was created by etching the surface of hypodermic tubing while the barbed assemblies were made using spring steel. Preliminary prototypes were tested first on silicone (10 Shore A) blocks to evaluate functionality. The textured design did not have enough surface area to create an appreciable difference in resistance between inserting and removing the syringe from the silicone. The barbed assemblies demonstrated satisfactory functionality and were then tested on a rack of beef ribs covered in a silicone sheet (to simulate skin). While the barbed design provided resistance to removal, the soft tissue was readily damaged, indicating that barbs or spines with greater surface area should be used. In some embodiments, nitinol spines may be used to accomplish this.

Aspect 6: Adjustable flange

The adjustable flange can prevent the needle assembly from penetrating too deeply into the pleural cavity after being deployed. This can be accomplished with an adjustable flange that slides down the bore of the hypodermic syringe to make contact with the skin of the patient's chest. Used in conjunction with the anchor, these design features can secure the needle assembly in place so it may not egress or ingress and potentially compromised safety and efficacy.

The adjustable flange was evaluated by testing compressive load resistance, ergonomics, and fatigue failure. The compressive load testing was performed by deploying the device into the simulated chest wall (made of silicone elastomer and urethane plastic) and applying an incremental compressive load to the modified Veress needle body until the locking mechanism of the adjustable flange fails (likely a simple ratchet design). In a representative example, a compressive load that the device resisted was approximately 25 lbs. Ergonomics can be adjusted for comfort and ease-of-use. Fatigue failure was assessed by repeatedly adjusting the flange the full length of its travel 100 times and monitoring for signs of mechanical failure. The device can be repositionable without compromising safety or efficacy.

A ratchet-style flange was developed. While the design performed as intended, it limited device dimensional minimization. In some configurations, alternative flange designs can circumvent the limitation. Leaflet and spring collar flange designs can provide greater positional freedom and allows future dimensional reduction.

Aspect 7: Color Indicator

Design: Body of the device can be made of a clear plastic so that a color indicator attached to the distal end of the internal cannula (furthest from the patient's body) can be monitored for pleural cavity penetration. As the needle assembly is inserted through the chest wall, a red indicator is visible until the cannula penetrates the pleural cavity and fully extends (so that the red indicator disappears).

The indicator was evaluated for function and visibility. Function was evaluated through repeatedly puncturing simulated tissue (silicone elastomer) 100 times (as the device must be capable of being repositioned without failure).

The indicator can be keyed to prevent rotation of the internal cannula during use.

Aspect 8: Augmented Flow Indicator

The sensitivity of the flow indicator can depend on several factors including surface area, diaphragm thickness, and/or diaphragm material stiffness. To enhance the sensitivity of the diaphragm, the surface area can be increased while the overall thickness can be decreased. The diaphragm could also be enhanced by improving visual contrast by adding a color changing component to the design. One design was based on creating a green dot that will appear and disappear based on diaphragm position, while the other design uses an expanding and collapsing red dimple.

Pigmented silicone parts were molded to assess the feasibility of the color contrast designs.

The preliminary design of the augmented flow indicator functioned by overlapping a translucent displacement diaphragm (yellow in color) with a blue umbrella valve to create a green visual que when the materials were in contact. The initial tests demonstrated proof of concept. In certain configurations, the flow indicator can be augmented by adding a colored dimple directly to the diaphragm that expands and collapses as the elastomer deforms.

Aspect 9: Integrated Guidewire Port

A silicone diaphragm can maintain a hermetic seal while allowing a guidewire to be passed from the exterior to the interior of the device. The port utilizes a compression fit and thick septum.

The hermetic seal of the device was evaluated at high and low pressure once the first functional prototypes were produced with and without wires present in the port. The ergonomics of the port was confirmed by passing a length of wire through the port and out the end of the blunt cannula.

The guidewire port was integrated into the body of the device between the cannula locking mechanism and displacement diaphragm so that all three elastomer components could be designed as a single part and overmolded upon a rigid polymer substrate. The port functioned appropriately under high/low pressure conditions.

Aspect 10: Optimal Interface

Depending on the methods used to achieve each of the specific aims, the interface between the enhanced modified Veress needle and tPTX device can be adjusted to mate appropriately.

The overall assembly was evaluated for ergonomics and compliance with expectations.

With the addition of a guidewire port, it was possible to combine the modified Veress needle with the tPTX device to create a single unit. The first functional prototype was reviewed and approved. Based on feedback, a few design modifications were made (most notably a reduction in hypodermic needle gauge) to more closely match the previously validated designs.

Commercial/Technical Problem(s) Addressed by the Experiment/Work Activity

The modified Veress needles disclosed herein can be used to address at least one or more of the following five shortcomings: 1) inadequate needle length, 2) small bore diameter (and subsequent restricted flow rates), 3) blind sharp needle insertion, 4) lack of visual or tactile feedback, and 5) plastic sheath composition. To further improve the safety and efficacy of the modified Veress needle, examples of suitable tPTX devices are disclosed. In comparison to other example tPTX devices disclosed herein, existing Veress needle assemblies: 1) have lower flow rates, 2) risk damaging viscera without the cannula secured in the extended position, 3) may allow the vented pleural cavity to equilibrate with atmospheric pressure (compromising organ function), 4) lack visual feedback for operator monitoring of decompression and sustained device function, and 5) are unable to attach or interface with medical devices or kits such as collection bags.

The tPTX devices disclosed herein can: 1) maintain the high flow rates established by the modified Veress needle, 2) protect viscera within the pleural cavity by bracing the internal cannula with a locking mechanism, 3) prevent atmospheric pressure from compromising organ function of the vented pleural cavity with the incorporation of a one-way valve, 4) provide a multifaceted flow indicator to monitor decompression and sustained device functionality, and 5) allow the needle assembly device to interface with a variety of medical kits/devices.

The disclosed tPTX devices improve upon safety and efficacy of existing modified Veress needle designs. As a result, the needle assemblies described herein have significant advantages over known Veress needles. One aspect of the tPTX device that may advance the device toward a marketable product is the multifaceted flow indicator. Conventional flow indicators demonstrate limited performance characteristics under the diverse flow and pressure conditions they may be exposed to under this application. The displacement flow indicator of the tPTX device provides feedback to operators beyond high or low flow conditions. It also indicates if a patient is misdiagnosed with tPTX, if the tPTX is successfully treated and resolved, or if the modified Veress needle is not correctly inserted for decompression.

In some embodiments, the modified Veress needle can include a flow indicator and a way to vent (e.g., via the diaphragm pump variant) the pleural cavity without use of a kit in the field (beneficial in resource-limited settings).

Example Interchangeable Augmented Flow Indicator Variations

Referring to FIG. 25, the augmented flow indicator with the red dimple can be advantageous because it provides greater visual contrast as the elastomer diaphragm expands and contracts. The augmented flow indicator that yields a green dot (overlapping a translucent yellow diaphragm and blue umbrella valve) can be less complex and expensive to produce.

Interchangeable Needle Assembly Anchor Designs

FIGS. 26 and 27 illustrate representative embodiments of interchangeable modified Veress needle anchor designs.

Interchangeable Locking Mechanisms

FIGS. 28A and 28B illustrate an example of a spring-loaded button including the locking member 124, which can be advantageous due to enhanced reliability, durability, and ergonomics. A cantilever locking mechanism can also be used, as shown in FIGS. 29A and 29B.

Interchangeable Adjustable Flange Designs

Figure 30:
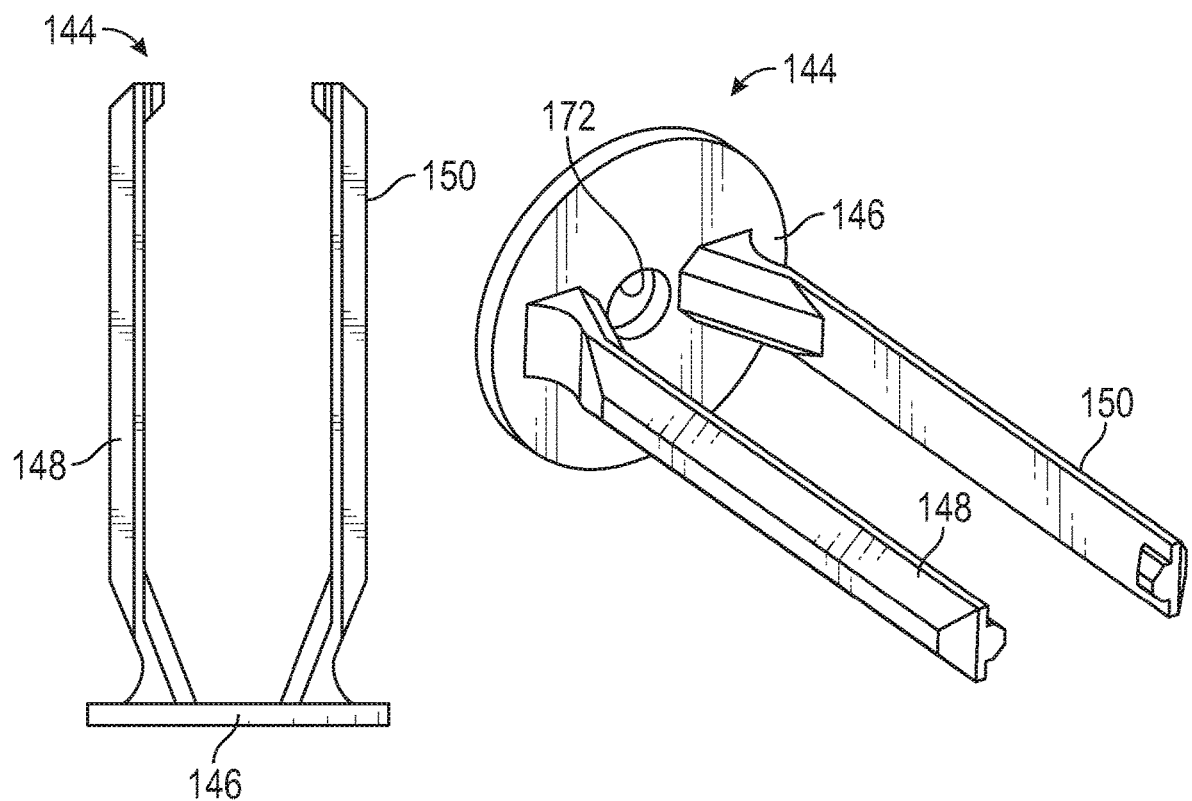
FIG. 30 illustrates a plan view and a perspective view of a travel-limiting assembly of the modified Veress needle of FIG. 9.

FIGS. 30 and 31 illustrate representative embodiments of interchangeable adjustable flange designs that can be used with any of the modified Veress needle embodiments described herein. The interlocking pin design exhibits improved stability, strength, and simplicity, and can include pin alignment features with pin slots incorporated into the body of the device.

In some embodiments, the interference fit design can have greater positional freedom to accommodate patient variability. In some embodiments, the design may be augmented with an elastomer overmold upon the leaflets to improve stability and strength. The leaflets can freely displace (outward) as the flange is moved forward, and bind if the flange is moved backward—resisting movement.

Flow Indicator Pump Conversion

FIG. 32 illustrates a flow indicator pump conversion. Adding a secondary valve (passive) to the device can allow the diaphragm to be used as a pump to evacuate the pleural cavity manually, which may improve or expedite treatment of tPTX in certain circumstances.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and do not exclude the presence of intermediate elements between the coupled or associated items, absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

What is claimed is:

1. A needle assembly, comprising:
   an outer cannula defining a lumen and having a proximal end portion and a distal end portion, the distal end portion of the outer cannula comprising a sharp bevel facilitating insertion of the needle assembly into a subject, the proximal end portion of the outer cannula being received in a housing;
   an inner cannula slidably disposed coaxially in the lumen of the outer cannula and being movable relative to the outer cannula between an extended position and a retracted position, the inner cannula defining a respective lumen and having a blunt distal end portion and a proximal end portion, the blunt distal end portion extending beyond the sharp bevel of the outer cannula whenever the inner cannula is in the extended position and being at least partially retracted within the lumen of the outer cannula whenever the inner cannula is in the retracted position, the proximal end portion of the inner cannula being received in the housing;
   a bias situated in the housing and coupled to the inner cannula and the outer cannula in a manner favoring automatic positioning of the inner cannula at the extended position unless the blunt distal end portion is experiencing a sufficient force to move the inner cannula to the retracted position;
   a valve located in the housing and in fluid communication with the lumen of the inner cannula and configured when the needle assembly is inserted into a subject to allow fluid to exit the subject through the inner cannula, and to prevent ingress of fluid into the subject when a pressure inside the subject is lower than an ambient pressure;
   wherein the valve includes a diaphragm configured as a one-way check valve, the diaphragm including an indicator configured as a protuberance; and
   wherein the housing further comprises a flexible membrane adjacent the protuberance such that the protuberance is visible to a user when the flexible membrane is in a contracted configuration, and not visible when the flexible membrane expands to an expanded configuration upon passage of fluid through the valve.

2. The needle assembly of claim 1, wherein the housing further comprises an introducer port in communication with the lumen of the inner cannula.

3. The needle assembly of claim 1, wherein the diaphragm comprises an expandable indicator configured to expand under the influence of fluid passing through the diaphragm.

4. The needle assembly of claim 1, wherein:
the flexible membrane is adjacent the diaphragm and movable between the expanded configuration and the contracted configuration with fluid flow through the diaphragm; and
the needle assembly further comprises a second one-way check valve downstream of the diaphragm and in fluid communication with the diaphragm such that movement of the flexible membrane by a user between the expanded configuration and the contracted configuration causes the diaphragm and the second one-way check valve to open and close to produce a pumping action.

5. The needle assembly of claim 1, further comprising a locking mechanism configured when activated to allow proximal motion of the inner cannula beyond a specified location.

6. The needle assembly of claim 5, wherein the locking mechanism comprises a locking member defining an opening through which the inner cannula can move when the locking mechanism is activated.

7. The needle assembly of claim 1, further comprising a travel-limiting assembly including a main body movable between an extended position and a retracted position and configured to contact the subject when the needle assembly is inserted into the subject to a specified depth.

8. The needle assembly of claim 7, wherein a surface of the main body comprises an adhesive to adhere the main body to the subject when the main body is in contact with the subject.

9. The needle assembly of claim 7, wherein the main body includes a spring collar configured to frictionally engage the outer cannula.

10. The needle assembly of claim 7, wherein the main body includes a plurality of tab portions configured to frictionally engage the outer cannula.

11. A method, comprising:
activating a locking mechanism of a Veress-type needle assembly to allow a biased inner cannula of the needle assembly to move from an extended position to a retracted position through an outer cannula through which the inner cannula is disposed, the outer cannula including a proximal end portion and a distal end portion, the proximal end portion of the outer cannula being coupled to a housing, the distal end portion of the outer cannula comprising a sharp bevel which is exposed when the inner cannula is in the retracted position, the needle assembly including a one-way check valve located in the housing and in fluid communication with a lumen of the inner cannula, the one-way check valve including a diaphragm, the diaphragm including an indicator configured as a protuberance, the housing further comprising a flexible membrane adjacent the protuberance such that the protuberance is visible to a user when the flexible membrane is in a non-deflected state and not visible when the flexible membrane expands to an expanded configuration upon passage of fluid through the one-way check valve;
advancing the needle assembly into a thoracic cavity of a living subject such that the inner cannula moves from the extended position to the retracted position through the outer cannula exposing the sharp bevel;
halting advancement of the needle assembly into the thoracic cavity when the inner cannula moves from the retracted position to the extended position.

12. The method of claim 11, further comprising allowing fluid to exit the thoracic cavity through the inner cannula and through the one-way check valve in fluid communication with the inner cannula.

13. The method of claim 11, wherein activating the locking mechanism further comprises depressing a locking member defining an opening such that the opening is coaxially aligned with the inner cannula.

14. The method of claim 11, further comprising, after halting advancement of the needle assembly, positioning a travel-limiting assembly to prevent further movement of the needle assembly into the thoracic cavity.

15. The method of claim 11, wherein a proximal end portion of the inner cannula provides a visual indication that the sharp bevel is exposed.

16. The method of claim 11, further comprising compressing and releasing the flexible membrane to pump fluid from the thoracic cavity of the living subject.

17. A method of making a needle assembly, comprising:
inserting an inner cannula through a lumen of an outer cannula such that the inner cannula is slidably disposed coaxially in the lumen of the outer cannula and movable relative to the outer cannula between an extended position and a retracted position, the outer cannula having a proximal end portion and a distal end portion, the distal end portion of the outer cannula comprising a sharp bevel facilitating insertion of the outer cannula into a subject, the inner cannula defining a respective lumen and having a blunt distal end portion and a proximal end portion, the blunt distal end portion extending beyond the sharp bevel of the outer cannula whenever the inner cannula is in the extended position and being at least partially retracted within the lumen of the outer cannula whenever the inner cannula is in the retracted position;
coupling a bias to the inner cannula in a manner favoring automatic positioning of the inner cannula at the extended position unless the blunt distal end portion is experiencing a sufficient force to move the inner cannula to the retracted position; and
situating the proximal end portion of the outer cannula, the proximal end portion of the inner cannula, and the bias in a housing such that a valve located in the housing is in fluid communication with the lumen of the inner cannula to allow fluid to exit a subject through the inner cannula when inserted into the subject, wherein the valve includes a diaphragm configured as a one-way check valve, the diaphragm further including an indicator configured as a protuberance, and wherein the housing further comprises a flexible membrane adjacent the protuberance such that the protuberance is visible to a user when the flexible membrane is in a non-deflected state, and not visible when the flexible membrane expands to an expanded configuration upon passage of fluid through the valve.

18. A needle assembly, comprising:
an outer cannula defining a lumen and having a proximal end portion and a distal end portion, the distal end portion of the outer cannula comprising a sharp bevel facilitating insertion of the needle assembly into a subject, the proximal end portion of the outer cannula being received in a housing;
an inner cannula slidably disposed coaxially in the lumen of the outer cannula and being movable relative to the outer cannula between an extended position and a retracted position, the inner cannula defining a respective lumen and having a blunt distal end portion and a proximal end portion, the blunt distal end portion of the inner cannula extending beyond the sharp bevel of the outer cannula whenever the inner cannula is in the extended position and being at least partially retracted within the lumen of the outer cannula whenever the inner cannula is in the retracted position, the proximal end portion of the inner cannula being received in the housing;

a bias situated in the housing and coupled to the inner cannula and the outer cannula in a manner favoring automatic positioning of the inner cannula at the extended position unless the blunt distal end portion is experiencing a sufficient force to move the inner cannula to the retracted position;

a valve located in the housing and in fluid communication with the lumen of the inner cannula and configured when inserted into a subject to allow fluid to exit the subject through the inner cannula, and to prevent ingress of fluid into the subject when a pressure inside the subject is lower than an ambient pressure, the valve including a diaphragm configured as a one-way check valve, the diaphragm including an indicator configured as a protuberance, the housing further comprising a flexible membrane adjacent the protuberance such that the protuberance is visible to a user when the flexible membrane is in a contracted configuration, and not visible when the flexible membrane expands to an expanded configuration upon passage of fluid through the valve;

a locking assembly including a locking member defining an opening through which the inner cannula can move when the locking assembly is activated;

an introducer port in communication with the inner cannula;

a travel-limiting assembly including a main body and a pair of arms configured to engage slots in the housing such that the position of the main body relative to the housing can be adjusted by a user and such that the main body can be positioned in contact with the subject; and a visual indicator coupled to and movable with the inner cannula to indicate to a user when the sharp bevel is exposed.

19. The needle assembly of claim 18, wherein:

the flexible membrane is adjacent the diaphragm and movable between the expanded configuration and the contracted configuration with fluid flow through the diaphragm; and the needle assembly further comprises a second one-way check valve downstream of the diaphragm and in fluid communication with the diaphragm such that movement of the flexible membrane by a user between the expanded configuration and the contracted configuration causes the diaphragm and the second one-way check valve to open and close to produce a pumping action.

* * * * *